US005315000A

United States Patent [19]

Degen

[11] Patent Number: 5,315,000

[45] Date of Patent: May 24, 1994

[54] GENE ENCODING FOR A L5/3 GROWTH FACTOR AND ITS CDNA

[75] Inventor: Sandra J. Degen, Cincinnati, Ohio

[73] Assignee: Children's Hospital Medical Center, Cincinnati, Ohio

[21] Appl. No.: 882,925

[22] Filed: May 14, 1992

[51] Int. Cl.$^5$ .................... C07H 15/12; C12N 15/00

[52] U.S. Cl. .............................. 536/23.5; 435/320.1; 435/69.1

[58] Field of Search ................ 536/23.45; 435/320.1, 435/69.0

[56] References Cited

PUBLICATIONS

Harbour et al. "Expression in Lung Cancer of a Trnscribed Sequence at the DNF 1552 Locus at Chromosome 3p21 "Anticancer Research 10 23-28 (1990).

Naylor et al. "Loss of heterozygosity of Chromosome 3p markers in small-cell using cancer" Nature 329 451-454 (1987).

Naylor et al "The DNF15S2 Locus at 3p21 Is Transcribed in Normal and Small Cell Lung Cancer," Genomics 4 355-361 (1989).

S. Degen: Isolation & Characterization of the Human Prothrombin Gene & Related Genes, Doctoral Thesis by S. Degen (1982).

S. Degen et al; Characterization of the Mouse cDNA & Gene Coding for a Hepatocyte Growth Factor-like Protein: Expression during Development; Biochemistry, 1991, 30 (pp. 9781-9791).

S. Han et al; Characterization of the DNF15S2 Locus on Human Chromosome 3: Identification of a Gene Coding for Four Kringle Domains with Homology to Hepatocyte Growth Factor, Biochemistry, 1991, 30 (pp. 9768-9780).

Michalopoulos et al: Hepatocyte Growth Factor, Hepatology vol. 15, No. 1, 1992, pp. 149-155.

Fausto et al: Regulation of Liver Growth: Protooncogens & Transforming Growth Factors; Laboratory Investigation, vol. 60, No. 1, p. 4, 1989.

Michalopoulos; Liver Regeneration: Molecular Mechanisms of Growth Control; The FASEB Journal, vol. 4, Feb. 1990.

Fusto: Liver Regeneration; ASLD Meeting 1991, pp. 149-160.

A. Skeel et al: Macrophage Stimulating Protein: Purification, Parttial Amino Acid Sequence, & Cellular Activity; The Journal of Experimental Medicine, vol. 173,. May, 1991, 1227-1234.

Fausto: Hepatocyte Growth Factor Receptor & The c-Met Oncogene Abstract; Hepatology, vol. 14, No. 4, Pt. 1, 1991, pp. 738-740.

*Primary Examiner*—Robert J. Hill, Jr.
*Assistant Examiner*—Shelly Guest Cermak
*Attorney, Agent, or Firm*—Wood Herron & Evans

[57] ABSTRACT

A growth factor protein similar in structure and function to hepatocyte growth factor has been discovered along with the DNA and cDNA coding for this in both the mouse and human. The DNA includes 18 exons and is homologous to DNA at the D3F15S2 locus on human chromosome 3; a region predicted to code for one or more tumor suppressor genes.

4 Claims, 1 Drawing Sheet

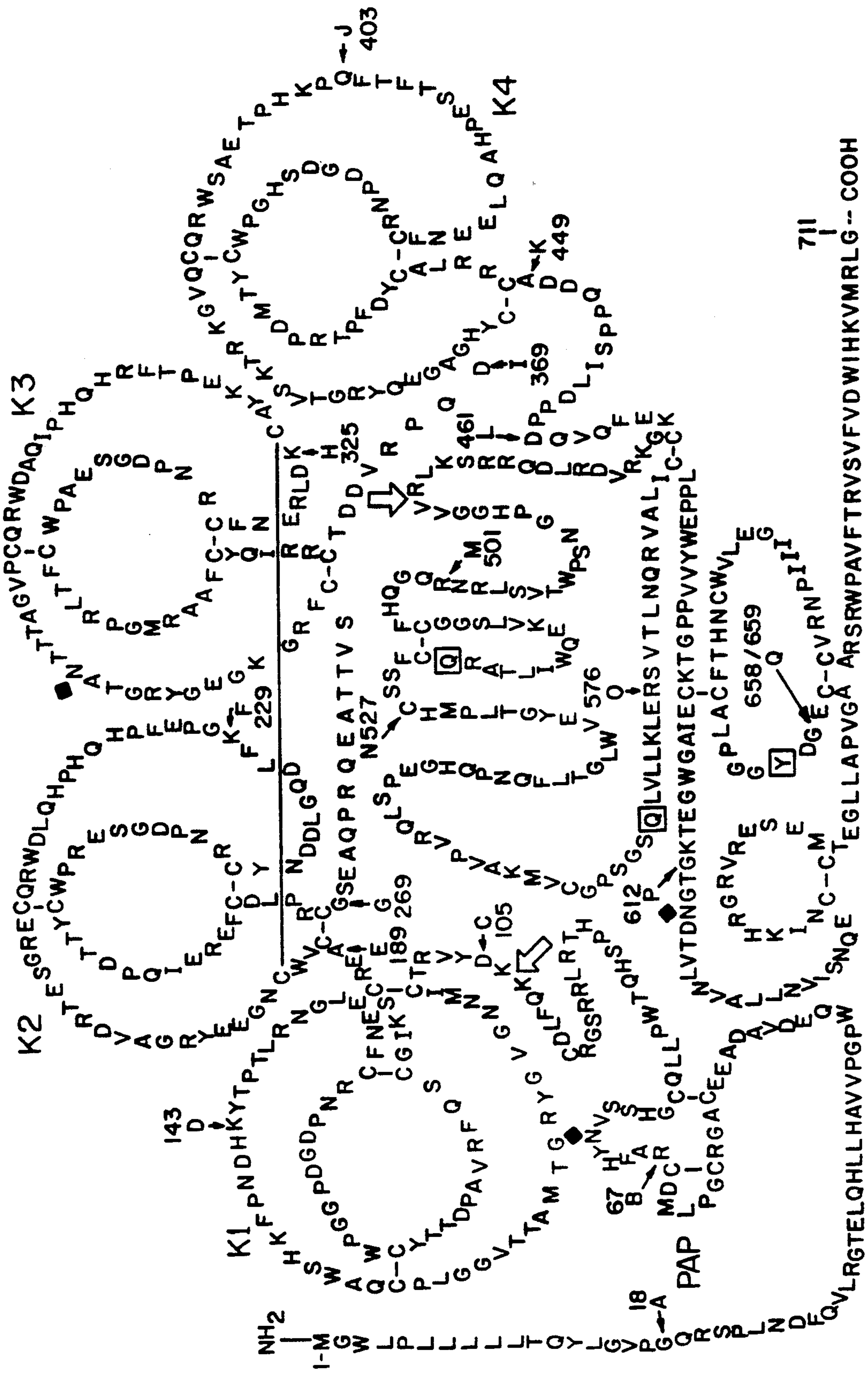
NH2
COOH
K1
K2
K3
K4
PAP
18
67
105
143
189
229
269
325
369
403
449
461
501
N527
576
612
658/659
711

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
( A ) LENGTH: 2219 base pairs
( B ) TYPE: nucleic acid
( C ) STRANDEDNESS: single
( D ) TOPOLOGY: linear ( i i ) MOLECULE TYPE: cDNA to mRNA ( i v ) ANTI-SENSE: no ( v i ) ORIGINAL SOURCE:
( A ) ORGANISM: human
( D ) DEVELOPMENTAL STAGE: fetal
( F ) TISSUE TYPE: liver -continued ( v i i ) IMMEDIATE SOURCE:
( A ) LIBRARY: cDNA
( B ) CLONE: #icrosoft Corp ( v i i i ) POSITION IN GENOME:
( A ) CHROMOSOME/SEGMENT: human 3p21/D3F15S2

( i x ) FEATURE:
( C ) IDENTIFICATION METHOD: experimental
( D ) OTHER INFORMATION: Includes five polymorphisms at the nucleotide level; one of which results in an amino acid substitution (nucleotide 619). Sequence ID NO:2: contains the identical sequence with the other polymorphic amino acid.

( x ) PUBLICATION INFORMATION:
( K ) RELEVANT RESIDUES IN SEQ ID NO: 1: FROM 1 TO 2219

( x i ) SEQUENCE DESCRIPTION: SEQ ID NO:1:

```
TC CTG CTG CTT CTG ACT CAA TAC TTA GGG GTC CCT GGG CAG CGC TCG         47
   Leu Leu Leu Leu Thr Gln Tyr Leu Gly Val Pro Gly Gln Arg Ser
   10                  15                  20

CCA TTG AAT GAC TTC CAA GTG CTC CGG GGC ACA GAG CTA CAG CAC CTG        95
Pro Leu Asn Asp Phe Gln Val Leu Arg Gly Thr Glu Leu Gln His Leu
25                  30                  35

CTA CAT GCG GTG GTG CCC GGG CCT TGG CAG GAG GAT GTG GCA GAT GCT       143
Leu His Ala Val Val Pro Gly Pro Trp Gln Glu Asp Val Ala Asp Ala
40                  45                  50

GAA GAG TGT GCT GGT CGC TGT GGG CCC TTA ATG GAC TGC CGG GCC TTC       191
Glu Glu Cys Ala Gly Arg Cys Gly Pro Leu Met Asp Cys Arg Ala Phe
55                  60                  65

CAC TAC AAC GTG AGC AGC CAT GGT TGC CAA CTG CTG CCA TGG ACT CAA       239
His Tyr Asn Val Ser Ser His Gly Cys Gln Leu Leu Pro Trp Thr Gln
70                  75                  80                  85

CAC TCG CCC CAC ACG AGG CTG CGG CGT TCT GGG CGC TGT GAC CTC TTC       287
His Ser Pro His Thr Arg Leu Arg Arg Ser Gly Arg Cys Asp Leu Phe
90                  95                 100

CAG AAG AAA GAC TAC GTA CGG ACC TGC ATC ATG AAC AAT GGG GTT GGG       335
Gln Lys Lys Asp Tyr Val Arg Thr Cys Ile Met Asn Asn Gly Val Gly
105                 110                 115

TAC CGG GGC ACC ATG GCC ACG ACC GTG GGT GGC CTG CCC TGC CAG GCT       383
Tyr Arg Gly Thr Met Ala Thr Thr Val Gly Gly Leu Pro Cys Gln Ala
120                 125                 130

TGG AGC CAC AAG TTC CCG AAT GAT CAC AAG TAC ACG CCC ACT CTC CGG       431
Trp Ser His Lys Phe Pro Asn Asp His Lys Tyr Thr Pro Thr Leu Arg
135                 140                 145

AAT GGC CTG GAA GAG AAC TTC TGC CGT AAC CCT GAT GGC GAC CCC GGA       479
Asn Gly Leu Glu Glu Asn Phe Cys Arg Asn Pro Asp Gly Asp Pro Gly
150                 155                 160                 165

GGT CCT TGG TGC TAC ACA ACA GAC CCT GCT GTG CGC TTC CAG AGC TGC       527
Gly Pro Trp Cys Tyr Thr Thr Asp Pro Ala Val Arg Phe Gln Ser Cys
170                 175                 180

GGC ATC AAA TCC TGC CGG GAG GCC GCG TGT GTC TGG TGC AAT GGC GAG       575
Gly Ile Lys Ser Cys Arg Glu Ala Ala Cys Val Trp Cys Asn Gly Glu
185                 190                 195

GAA TAC CGC GGC GCG GTA GAC CGC ACG GAG TCA GGG CGC GAG TGC CAG       623
Glu Tyr Arg Gly Ala Val Asp Arg Thr Glu Ser Gly Arg Glu Cys Gln
200                 205                 210

CGC TGG GAT CTT CAG CAC CCG CAC CAG CAC CCC TTC GAG CCG GGC AAG       671
Arg Trp Asp Leu Gln His Pro His Gln His Pro Phe Glu Pro Gly Lys
215                 220                 225

TTC CTC GAC CAA GGT CTG GAC GAC AAC TAT TGC CGG AAT CCT GAC GGC       719
Phe Leu Asp Gln Gly Leu Asp Asp Asn Tyr Cys Arg Asn Pro Asp Gly
230                 235                 240                 245

TCC GAG CGG CCA TGG TGC TAC ACT ACG GAT CCG CAG ATC GAG CGA GAG       767
```

-continued

Ser Glu Arg Pro Trp Cys Tyr Thr Thr Asp Pro Gln Ile Glu Arg Glu
250 255 260

TTC TGT GAC CTC CCC CGC TGC GGG TCC GAG GCA CAG CCC CGC CAA GAG 815
Phe Cys Asp Leu Pro Arg Cys Gly Ser Glu Ala Gln Pro Arg Gln Glu
265 270 275

GCC ACA ACT GTC AGC TGC TTC CGC GGG AAG GGT GAG GGC TAC CGG GGC 863
Ala Thr Thr Val Ser Cys Phe Arg Gly Lys Gly Glu Gly Tyr Arg Gly
280 285 290

ACA GCC AAT ACC ACC ACT GCG GGC GTA CCT TGC CAG CGT TGG GAC GCG 911
Thr Ala Asn Thr Thr Thr Ala Gly Val Pro Cys Gln Arg Trp Asp Ala
295 300 305

CAA ATC CCT CAT CAG CAC CGA TTT ACG CCA GAA AAA TAC GCG TGC AAA 959
Gln Ile Pro His Gln His Arg Phe Thr Pro Glu Lys Tyr Ala Cys Lys
310 315 320 325

GAC CTT CGG GAG AAC TTC TGC CGG AAC CCC GAC GGC TCA GAG GCG CCC 1007
Asp Leu Arg Glu Asn Phe Cys Arg Asn Pro Asp Gly Ser Glu Ala Pro
330 335 340

TGG TGC TTC ACA CTG CGG CCC GGC ATG CGC GCG GCC TTT TGC TAC CAG 1055
Trp Cys Phe Thr Leu Arg Pro Gly Met Arg Ala Ala Phe Cys Tyr Gln
345 350 355

ATC CGG CGT TGT ACA GAC GAC GTG CGG CCC CAG GAC TGC TAC CAC GGC 1103
Ile Arg Arg Cys Thr Asp Asp Val Arg Pro Gln Asp Cys Tyr His Gly
360 365 370

GCA GGG GAG CAG TAC CGC GGC ACG GTC AGC AAG ACC CGC AAG GGT GTC 1151
Ala Gly Glu Gln Tyr Arg Gly Thr Val Ser Lys Thr Arg Lys Gly Val
375 380 385

CAG TGC CAG CGC TGG TCC GCT GAG ACG CCG CAC AAG CCG CAG TTC ACG 1199
Gln Cys Gln Arg Trp Ser Ala Glu Thr Pro His Lys Pro Gln Phe Thr
390 395 400 405

TTT ACC TCC GAR CCG CAT GCA CAA CTG GAG GAG AAC TTC TGC CGG AAC 1247
Phe Thr Ser Glu Pro His Ala Gln Leu Glu Glu Asn Phe Cys Arg Asn
410 415 420

CCA GAT GGG GAT AGC CAT GGG CCC TGG TGC TAC ACG ATG GAC CCA AGG 1295
Pro Asp Gly Asp Ser His Gly Pro Trp Cys Tyr Thr Met Asp Pro Arg
425 430 435

ACC CCA TTC GAC TAC TGT GCC CTG CGA CGC TGC GCT GAT GAC CAG CCG 1343
Thr Pro Phe Asp Tyr Cys Ala Leu Arg Arg Cys Ala Asp Asp Gln Pro
440 445 450

CCA TCA ATC CTG GAC CCC CCA GAC CAG GTG CAG TTT GAG AAG TGT GGC 1391
Pro Ser Ile Leu Asp Pro Pro Asp Gln Val Gln Phe Glu Lys Cys Gly
455 460 465

AAG AGG GTG GAT CGG CTG GAT CAG CGG CGT TCC AAG CTG CGC GTG GTT 1439
Lys Arg Val Asp Arg Leu Asp Gln Arg Arg Ser Lys Leu Arg Val Val
470 475 480 485

GGG GGC CAT CCG GGC AAC TCA CCC TGG ACA GTC AGC TTG CGG AAT CGG 1487
Gly Gly His Pro Gly Asn Ser Pro Trp Thr Val Ser Leu Arg Asn Arg
490 495 500

CAG GGC CAG CAT TTC TGC GGG GGG TCT CTA GTG AAG GAG CAG TGG ATA 1535
Gln Gly Gln His Phe Cys Gly Gly Ser Leu Val Lys Glu Gln Trp Ile
505 510 515

CTG ACT GCC CGG CAG TGC TTC TCC TCC TGC CAT ATG CCT CTC ACG GGC 1583
Leu Thr Ala Arg Gln Cys Phe Ser Ser Cys His Met Pro Leu Thr Gly
520 525 530

TAT GAG GTA TGG TTG GGC ACC CTG TTC CAG AAC CCA CAG CAT GGA GAG 1631
Tyr Glu Val Trp Leu Gly Thr Leu Phe Gln Asn Pro Gln His Gly Glu
535 540 545

CCA AGC CTA CAG CGG GTC CCA GTA GCC AAG ATG GTG TGT GGG CCC TCA 1679
Pro Ser Leu Gln Arg Val Pro Val Ala Lys Met Val Cys Gly Pro Ser
550 555 560 565

GGC TCC CAG CTT GTC CTG CTC AAG CTG GAG AGA TCT GTG ACC CTG AAC 1727
Gly Ser Gln Leu Val Leu Leu Lys Leu Glu Arg Ser Val Thr Leu Asn
570 575 580

-continued

CAG CGY GTG GCC CTG ATC TGC CTG CCC CCT GAA TGG TAT GTG GTG CCT 1775
Gln Arg Val Ala Leu Ile Cys Leu Pro Pro Glu Trp Tyr Val Val Pro
585 590 595

CCA GGG ACC AAG TGT GAG ATT GCA GGC TGG GGT GAG ACC AAA GGT ACG 1823
Pro Gly Thr Lys Cys Glu Ile Ala Gly Trp Gly Glu Thr Lys Gly Thr
600 605 610

GGT AAT GAC ACA GTC CTA AAT GTG GCC TTG CTG AAT GTC ATC TCC AAC 1871
Gly Asn Asp Thr Val Leu Asn Val Ala Leu Leu Asn Val Ile Ser Asn
615 620 625

CAG GAG TGT AAC ATC AAR CAC CGA GGA CGT GTG CGK GAG AGT GAG ATG 1919
Gln Glu Cys Asn Ile Lys His Arg Gly Arg Val Arg Glu Ser Glu Met
630 635 640 645

TGC ACT GAG GGA CTG TTG GCC CCT GTG GGG GCC TGT GAG GGT GAC TAC 1967
Cys Thr Glu Gly Leu Leu Ala Pro Val Gly Ala Cys Glu Gly Asp Tyr
650 655 660

GGG GGC CCA CTT GCC TGC TTT ACC CAC AAC TGC TGG GTC CTG GAA GGA 2015
Gly Gly Pro Leu Ala Cys Phe Thr His Asn Cys Trp Val Leu Glu Gly
665 670 675

ATT ATA ATC CCC AAC CGA GTA TGC GCA AGG TCC CGC TGG CCA GCT GTC 2063
Ile Ile Ile Pro Asn Arg Val Cys Ala Arg Ser Arg Trp Pro Ala Val
680 685 690

TTC ACG CGT GTC TCT GTG TTT GTG GAC TGG ATT CAC AAG GTC ATG AGA 2111
Phe Thr Arg Val Ser Val Phe Val Asp Trp Ile His Lys Val Met Arg
695 700 705

CTG GGT TAGGCCCAGC CTTGATGCCA TATGCCTTGG GGAGGACAAA ACTTCTTGTC 2167
Leu Gly
710

AGACATAAAG CCATGTTTCC TCTTTATGCC TGTAAAAAAA AAAAAAAAAA AA 2219

( 2 ) INFORMATION FOR SEQ ID NO:2:

( i ) SEQUENCE CHARACTERISTICS:
( A ) LENGTH: 2219 base pairs
( B ) TYPE: nucleic acid
( C ) STRANDEDNESS: single
( D ) TOPOLOGY: linear ( i i ) MOLECULE TYPE: cDNA to mRNA ( i v ) ANTI-SENSE: no ( v i ) ORIGINAL SOURCE:
( A ) ORGANISM: human
( D ) DEVELOPMENTAL STAGE: fetal
( F ) TISSUE TYPE: liver ( v i i ) IMMEDIATE SOURCE:
( A ) LIBRARY: cDNA
( B ) CLONE: #icrosoft Corp ( v i i i ) POSITION IN GENOME:
( A ) CHROMOSOME/SEGMENT: human 3p21/D3F15S2

( i x ) FEATURE:
( C ) IDENTIFICATION METHOD: experimental
( D ) OTHER INFORMATION: Includes five polymorphisms at the nucleotide level; one of which results in an amino acid substitution (nucleotide 619). Sequence ID NO:1: contains the identical sequence with the other polymorphic amino acid.

( x ) PUBLICATION INFORMATION:
( K ) RELEVANT RESIDUES IN SEQ ID NO: 2: FROM 1 TO 2219

( x i ) SEQUENCE DESCRIPTION: SEQ ID NO:2:

TC CTG CTG CTT CTG ACT CAA TAC TTA GGG GTC CCT GGG CAG CGC TCG 47
Leu Leu Leu Leu Thr Gln Tyr Leu Gly Val Pro Gly Gln Arg Ser
10 15 20

CCA TTG AAT GAC TTC CAA GTG CTC CGG GGC ACA GAG CTA CAG CAC CTG 95

-continued

Pro Leu Asn Asp Phe Gln Val Leu Arg Gly Thr Glu Leu Gln His Leu
25 30 35

CTA CAT GCG GTG GTG CCC GGG CCT TGG CAG GAG GAT GTG GCA GAT GCT 143
Leu His Ala Val Val Pro Gly Pro Trp Gln Glu Asp Val Ala Asp Ala
40 45 50

GAA GAG TGT GCT GGT CGC TGT GGG CCC TTA ATG GAC TGC CGG GCC TTC 191
Glu Glu Cys Ala Gly Arg Cys Gly Pro Leu Met Asp Cys Arg Ala Phe
55 60 65

CAC TAC AAC GTG AGC AGC CAT GGT TGC CAA CTG CTG CCA TGG ACT CAA 239
His Tyr Asn Val Ser Ser His Gly Cys Gln Leu Leu Pro Trp Thr Gln
70 75 80 85

CAC TCG CCC CAC ACG AGG CTG CGG CGT TCT GGG CGC TGT GAC CTC TTC 287
His Ser Pro His Thr Arg Leu Arg Arg Ser Gly Arg Cys Asp Leu Phe
90 95 100

CAG AAG AAA GAC TAC GTA CGG ACC TGC ATC ATG AAC AAT GGG GTT GGG 335
Gln Lys Lys Asp Tyr Val Arg Thr Cys Ile Met Asn Asn Gly Val Gly
105 110 115

TAC CGG GGC ACC ATG GCC ACG ACC GTG GGT GGC CTG CCC TGC CAG GCT 383
Tyr Arg Gly Thr Met Ala Thr Thr Val Gly Gly Leu Pro Cys Gln Ala
120 125 130

TGG AGC CAC AAG TTC CCG AAT GAT CAC AAG TAC ACG CCC ACT CTC CGG 431
Trp Ser His Lys Phe Pro Asn Asp His Lys Tyr Thr Pro Thr Leu Arg
135 140 145

AAT GGC CTG GAA GAG AAC TTC TGC CGT AAC CCT GAT GGC GAC CCC GGA 479
Asn Gly Leu Glu Glu Asn Phe Cys Arg Asn Pro Asp Gly Asp Pro Gly
150 155 160 165

GGT CCT TGG TGC TAC ACA ACA GAC CCT GCT GTG CGC TTC CAG AGC TGC 527
Gly Pro Trp Cys Tyr Thr Thr Asp Pro Ala Val Arg Phe Gln Ser Cys
170 175 180

GGC ATC AAA TCC TGC CGG GAG GCC GCG TGT GTC TGG TGC AAT GGC GAG 575
Gly Ile Lys Ser Cys Arg Glu Ala Ala Cys Val Trp Cys Asn Gly Glu
185 190 195

GAA TAC CGC GGC GCG GTA GAC CGC ACG GAG TCA GGG CGC GAG TTC CAG 623
Glu Tyr Arg Gly Ala Val Asp Arg Thr Glu Ser Gly Arg Glu Phe Gln
200 205 210

CGC TGG GAT CTT CAG CAC CCG CAC CAG CAC CCC TTC GAG CCG GGC AAG 671
Arg Trp Asp Leu Gln His Pro His Gln His Pro Phe Glu Pro Gly Lys
215 220 225

TTC CTC GAC CAA GGT CTG GAC GAC AAC TAT TGC CGG AAT CCT GAC GGC 719
Phe Leu Asp Gln Gly Leu Asp Asp Asn Tyr Cys Arg Asn Pro Asp Gly
230 235 240 245

TCC GAG CGG CCA TGG TGC TAC ACT ACG GAT CCG CAG ATC GAG CGA GAG 767
Ser Glu Arg Pro Trp Cys Tyr Thr Thr Asp Pro Gln Ile Glu Arg Glu
250 255 260

TTC TGT GAC CTC CCC CGC TGC GGG TCC GAG GCA CAG CCC CGC CAA GAG 815
Phe Cys Asp Leu Pro Arg Cys Gly Ser Glu Ala Gln Pro Arg Gln Glu
265 270 275

GCC ACA ACT GTC AGC TGC TTC CGC GGG AAG GGT GAG GGC TAC CGG GGC 863
Ala Thr Thr Val Ser Cys Phe Arg Gly Lys Gly Glu Gly Tyr Arg Gly
280 285 290

ACA GCC AAT ACC ACC ACT GCG GGC GTA CCT TGC CAG CGT TGG GAC GCG 911
Thr Ala Asn Thr Thr Thr Ala Gly Val Pro Cys Gln Arg Trp Asp Ala
295 300 305

CAA ATC CCT CAT CAG CAC CGA TTT ACG CCA GAA AAA TAC GCG TGC AAA 959
Gln Ile Pro His Gln His Arg Phe Thr Pro Glu Lys Tyr Ala Cys Lys
310 315 320 325

GAC CTT CGG GAG AAC TTC TGC CGG AAC CCC GAC GGC TCA GAG GCG CCC 1007
Asp Leu Arg Glu Asn Phe Cys Arg Asn Pro Asp Gly Ser Glu Ala Pro
330 335 340

TGG TGC TTC ACA CTG CGG CCC GGC ATG CGC GCG GCC TTT TGC TAC CAG 1055
Trp Cys Phe Thr Leu Arg Pro Gly Met Arg Ala Ala Phe Cys Tyr Gln
345 350 355

-continued

ATC CGG CGT TGT ACA GAC GAC GTG CGG CCC CAG GAC TGC TAC CAC GGC 1103
Ile Arg Arg Cys Thr Asp Asp Val Arg Pro Gln Asp Cys Tyr His Gly
360 365 370

GCA GGG GAG CAG TAC CGC GGC ACG GTC AGC AAG ACC CGC AAG GGT GTC 1151
Ala Gly Glu Gln Tyr Arg Gly Thr Val Ser Lys Thr Arg Lys Gly Val
375 380 385

CAG TGC CAG CGC TGG TCC GCT GAG ACG CCG CAC AAG CCG CAG TTC ACG 1199
Gln Cys Gln Arg Trp Ser Ala Glu Thr Pro His Lys Pro Gln Phe Thr
390 395 400 405

TTT ACC TCC GAR CCG CAT GCA CAA CTG GAG GAG AAC TTC TGC CGG AAC 1247
Phe Thr Ser Glu Pro His Ala Gln Leu Glu Glu Asn Phe Cys Arg Asn
410 415 420

CCA GAT GGG GAT AGC CAT GGG CCC TGG TGC TAC ACG ATG GAC CCA AGG 1295
Pro Asp Gly Asp Ser His Gly Pro Trp Cys Tyr Thr Met Asp Pro Arg
425 430 435

ACC CCA TTC GAC TAC TGT GCC CTG CGA CGC TGC GCT GAT GAC CAG CCG 1343
Thr Pro Phe Asp Tyr Cys Ala Leu Arg Arg Cys Ala Asp Asp Gln Pro
440 445 450

CCA TCA ATC CTG GAC CCC CCA GAC CAG GTG CAG TTT GAG AAG TGT GGC 1391
Pro Ser Ile Leu Asp Pro Pro Asp Gln Val Gln Phe Glu Lys Cys Gly
455 460 465

AAG AGG GTG GAT CGG CTG GAT CAG CGG CGT TCC AAG CTG CGC GTG GTT 1439
Lys Arg Val Asp Arg Leu Asp Gln Arg Arg Ser Lys Leu Arg Val Val
470 475 480 485

GGG GGC CAT CCG GGC AAC TCA CCC TGG ACA GTC AGC TTG CGG AAT CGG 1487
Gly Gly His Pro Gly Asn Ser Pro Trp Thr Val Ser Leu Arg Asn Arg
490 495 500

CAG GGC CAG CAT TTC TGC GGG GGG TCT CTA GTG AAG GAG CAG TGG ATA 1535
Gln Gly Gln His Phe Cys Gly Gly Ser Leu Val Lys Glu Gln Trp Ile
505 510 515

CTG ACT GCC CGG CAG TGC TTC TCC TCC TGC CAT ATG CCT CTC ACG GGC 1583
Leu Thr Ala Arg Gln Cys Phe Ser Ser Cys His Met Pro Leu Thr Gly
520 525 530

TAT GAG GTA TGG TTG GGC ACC CTG TTC CAG AAC CCA CAG CAT GGA GAG 1631
Tyr Glu Val Trp Leu Gly Thr Leu Phe Gln Asn Pro Gln His Gly Glu
535 540 545

CCA AGC CTA CAG CGG GTC CCA GTA GCC AAG ATG GTG TGT GGG CCC TCA 1679
Pro Ser Leu Gln Arg Val Pro Val Ala Lys Met Val Cys Gly Pro Ser
550 555 560 565

GGC TCC CAG CTT GTC CTG CTC AAG CTG GAG AGA TCT GTG ACC CTG AAC 1727
Gly Ser Gln Leu Val Leu Leu Lys Leu Glu Arg Ser Val Thr Leu Asn
570 575 580

CAG CGY GTG GCC CTG ATC TGC CTG CCC CCT GAA TGG TAT GTG GTG CCT 1775
Gln Arg Val Ala Leu Ile Cys Leu Pro Pro Glu Trp Tyr Val Val Pro
585 590 595

CCA GGG ACC AAG TGT GAG ATT GCA GGC TGG GGT GAG ACC AAA GGT ACG 1823
Pro Gly Thr Lys Cys Glu Ile Ala Gly Trp Gly Glu Thr Lys Gly Thr
600 605 610

GGT AAT GAC ACA GTC CTA AAT GTG GCC TTG CTG AAT GTC ATC TCC AAC 1871
Gly Asn Asp Thr Val Leu Asn Val Ala Leu Leu Asn Val Ile Ser Asn
615 620 625

CAG GAG TGT AAC ATC AAR CAC CGA GGA CGT GTG CGK GAG AGT GAG ATG 1919
Gln Glu Cys Asn Ile Lys His Arg Gly Arg Val Arg Glu Ser Glu Met
630 635 640 645

TGC ACT GAG GGA CTG TTG GCC CCT GTG GGG GCC TGT GAG GGT GAC TAC 1967
Cys Thr Glu Gly Leu Leu Ala Pro Val Gly Ala Cys Glu Gly Asp Tyr
650 655 660

GGG GGC CCA CTT GCC TGC TTT ACC CAC AAC TGC TGG GTC CTG GAA GGA 2015
Gly Gly Pro Leu Ala Cys Phe Thr His Asn Cys Trp Val Leu Glu Gly
665 670 675

ATT ATA ATC CCC AAC CGA GTA TGC GCA AGG TCC CGC TGG CCA GCT GTC 2063

-continued

```
Ile Ile Ile Pro Asn Arg Val Cys Ala Arg Ser Arg Trp Pro Ala Val
680                 685                 690

TTC ACG CGT GTC TCT GTG TTT GTG GAC TGG ATT CAC AAG GTC ATG AGA      2111
Phe Thr Arg Val Ser Val Phe Val Asp Trp Ile His Lys Val Met Arg
695                 700                 705

CTG GGT TAGGCCCAGC CTTGATGCCA TATGCCTTGG GGAGGACAAA ACTTCTTGTC       2167
Leu Gly
710

AGACATAAAG CCATGTTTCC TCTTTATGCC TGTAAAAAAA AAAAAAAAAA AA            2219
```

( 2 ) INFORMATION FOR SEQ ID NO:3:

( i ) SEQUENCE CHARACTERISTICS:
( A ) LENGTH: 2021 base pairs
( B ) TYPE: nucleic acid
( C ) STRANDEDNESS: single
( D ) TOPOLOGY: linear ( i i ) MOLECULE TYPE: cDNA to mRNA ( i v ) ANTI-SENSE: no ( v i ) ORIGINAL SOURCE:
( A ) ORGANISM: human
( D ) DEVELOPMENTAL STAGE: fetal
( F ) TISSUE TYPE: liver ( v i i ) IMMEDIATE SOURCE:
( A ) LIBRARY: cDNA
( B ) CLONE: #Microsoft Corp ( v i i i ) POSITION IN GENOME:
( A ) CHROMOSOME/SEGMENT: human 3p21/D3F15S2

( i x ) FEATURE:
( C ) IDENTIFICATION METHOD: experimental
( D ) OTHER INFORMATION: This sequence is a variant where two regions were found to be deleted when compared to SEQ ID NO:1.

( x ) PUBLICATION INFORMATION:
( K ) RELEVANT RESIDUES IN SEQ ID NO:3: FROM 1 TO 2021

( x i ) SEQUENCE DESCRIPTION: SEQ ID NO:3:

```
A TGC TTA GGG GTC CCT GGG CAG CGC TCG CCA TTG AAT GAC TTC CAA          46
  Cys Leu Gly Val Pro Gly Gln Arg Ser Pro Leu Asn Asp Phe Gln
  15                  20                  25

GTG CTC CGG GGC ACA GAG CTA CAG CAC CTG CTA CAT GCG GTG GTG CCC        94
Val Leu Arg Gly Thr Glu Leu Gln His Leu Leu His Ala Val Val Pro
30                  35                  40

GGG CCT TGG CAG GAG GAT GTG GCA GAT GCT GAA GAG TGT GCT GGT CGC       142
Gly Pro Trp Gln Glu Asp Val Ala Asp Ala Glu Glu Cys Ala Gly Arg
45                  50                  55

TGT GGG CCC TTA ATG GAC TGC CGG GCC TTC CAC TAC AAC GTG AGC AGC       190
Cys Gly Pro Leu Met Asp Cys Arg Ala Phe His Tyr Asn Val Ser Ser
60                  65                  70                  75

CAT GGT TGC CAA CTG CTG CCA TGG ACT CAA CAC TCG CCC CAC ACG AGG       238
His Gly Cys Gln Leu Leu Pro Trp Thr Gln His Ser Pro His Thr Arg
80                  85                  90

CTG CGG CGT TCT GGG CGC TGT GAC CTC TTC CAG AAG AAA GAC TAC GTA       286
Leu Arg Arg Ser Gly Arg Cys Asp Leu Phe Gln Lys Lys Asp Tyr Val
95                  100                 105

CGG ACC TGC ATC ATG AAC AAT GGG GTT GGG TAC CGG GGC ACC ATG GCC       334
Arg Thr Cys Ile Met Asn Asn Gly Val Gly Tyr Arg Gly Thr Met Ala
110                 115                 120

ACG ACC GTG GGT GGC CTG CCC TGC CAG GCT TGG AGC CAC AAG TTC CCG       382
Thr Thr Val Gly Gly Leu Pro Cys Gln Ala Trp Ser His Lys Phe Pro
125                 130                 135

AAT GAT CAC AAG TAC ACG CCC ACT CTC CGG AAT GGC CTG GAA GAG AAC       430
```

-continued

Asn Asp His Lys Tyr Thr Pro Thr Leu Arg Asn Gly Leu Glu Glu Asn
140 145 150 155

TTC TGC CGT AAC CCT GAT GGC GAC CCC GGA GGT CCT TGG TGC TAC ACA 478
Phe Cys Arg Asn Pro Asp Gly Asp Pro Gly Gly Pro Trp Cys Tyr Thr
160 165 170

ACA GAC CCT GCT GTG CGC TTC CAG AGC TGC GGC ATC AAA TCC TGC CGG 526
Thr Asp Pro Ala Val Arg Phe Gln Ser Cys Gly Ile Lys Ser Cys Arg
175 180 185

GAG GCC GCG TGT GTC TGG TGC AAT GGC GAG GAA TAC CGC GGC GCG GTA 574
Glu Ala Ala Cys Val Trp Cys Asn Gly Glu Glu Tyr Arg Gly Ala Val
190 195 200

GAC CGC ACG GAG TCA GGG CGC GAG TGC CAG CGC TGG GAT CTT CAG CAC 622
Asp Arg Thr Glu Ser Gly Arg Glu Cys Gln Arg Trp Asp Leu Gln His
205 210 215

CCG CAC CAG CAC CCC TTC GAG CCG GGC AAG TTC CTC GAC CAA GGT CTG 670
Pro His Gln His Pro Phe Glu Pro Gly Lys Phe Leu Asp Gln Gly Leu
220 225 230 235

GAC GAC AAC TAT TGC CGG AAT CCT GAC GGC TCC GAG CGG CCA TGG TGC 718
Asp Asp Asn Tyr Cys Arg Asn Pro Asp Gly Ser Glu Arg Pro Trp Cys
240 245 250

TAC ACT ACG GAT CCG CAG ATC GAG CGA GAG TTC TGT GAC CTC CCC CGC 766
Tyr Thr Thr Asp Pro Gln Ile Glu Arg Glu Phe Cys Asp Leu Pro Arg
255 260 265

TGC GGG TCC GAG GCA CAG CCC CGC CAA GAG GCC ACA ACT GTC AGC TGC 814
Cys Gly Ser Glu Ala Gln Pro Arg Gln Glu Ala Thr Thr Val Ser Cys
270 275 280

TTC CGC GGG AAG GGT GAG GGC TAC CGG GGC ACA GCC AAT ACC ACC ACT 862
Phe Arg Gly Lys Gly Glu Gly Tyr Arg Gly Thr Ala Asn Thr Thr Thr
285 290 295

GCG GGC GTA CCT TGC CAG CGT TGG GAC GCG CAA ATC CCT CAT CAG CAC 910
Ala Gly Val Pro Cys Gln Arg Trp Asp Ala Gln Ile Pro His Gln His
300 305 310 315

CGA TTT ACG CCA GAA AAA TAC GCG TGC AAA GAC CTT CGG GAG AAC TTC 958
Arg Phe Thr Pro Glu Lys Tyr Ala Cys Lys Asp Leu Arg Glu Asn Phe
320 325 330

TGC CGG AAC CCC GAC GGC TCA GAG GCG CCC TGG TGC TTC ACA CTG CGG 1006
Cys Arg Asn Pro Asp Gly Ser Glu Ala Pro Trp Cys Phe Thr Leu Arg
335 340 345

CCC GGC ATG CGC GCG GCC TTT TGC TAC CAG ATC CGG CGT TGT ACA GAC 1054
Pro Gly Met Arg Ala Ala Phe Cys Tyr Gln Ile Arg Arg Cys Thr Asp
350 355 360

GAC GTG CGG CCC CAG GAC TGC TAC CAC GGC GCA GGG GAG CAG TAC CGC 1102
Asp Val Arg Pro Gln Asp Cys Tyr His Gly Ala Gly Glu Gln Tyr Arg
365 370 375

GGC ACG GTC AGC AAG ACC CGC AAG GGT GTC CAG TGC CAG CGC TGG TCC 1150
Gly Thr Val Ser Lys Thr Arg Lys Gly Val Gln Cys Gln Arg Trp Ser
380 385 390 395

GCT GAG ACG CCG CAC AAG CCG CAG TTC ACG TTT ACC TCC GAA CCG CAT 1198
Ala Glu Thr Pro His Lys Pro Gln Phe Thr Phe Thr Ser Glu Pro His
400 405 410

GCA CAA CTG GAG GAG AAC TTC TGC CGG AAC CCA GAT GGG GAT AGC CAT 1246
Ala Gln Leu Glu Glu Asn Phe Cys Arg Asn Pro Asp Gly Asp Ser His
415 420 425

GGG CCC TGG TGC TAC ACG ATG GAC CCA AGG ACC CCA TTC GAC TAC TGT 1294
Gly Pro Trp Cys Tyr Thr Met Asp Pro Arg Thr Pro Phe Asp Tyr Cys
430 435 440

GCC CTG CGA CGC TGC GCT GAT GAC CAG CCG CCA TCA ATC CTG GAC CCC 1342
Ala Leu Arg Arg Cys Ala Asp Asp Gln Pro Pro Ser Ile Leu Asp Pro
445 450 455

CCA GGC AGG GCC AGC ATT TCT GCG GGG GGT CTC TAGTGAAGGA GCAGTGGATA 1395
Pro Gly Arg Ala Ser Ile Ser Ala Gly Gly Leu
460 465 470

-continued

```
CTGACTGCCC GGCAGTGCTT CTCCTCCTGA ACCCACAGCA TGGAGAGCCA AGCCTACAGC   1455
GGGTCCCAGT AGCCAAGATG GTGTGTGGGC CCTCAGGCTC CCAGCTTGTC CTGCTCAAGC   1515
TGGAGAGATC TGTGACCCTG AACCAGCGCG TGGCCCTGAT CTGCCTGCCC CCTGAATGGT   1575
ATGTGGTGCC TCCAGGGACC AAGTGTGAGA TTGCAGGCTG GGGTGAGACC AAAGGTACGG   1635
GTAATGACAC AGTCCTAAAT GTGGCCTTGC TGAATGTCAT CTCCAACCAG GAGTGTAACA   1695
TCAAGCACCG AGGACGTGTG CGTGAGAGTG AGATGTGCAC TGAGGGACTG TTGGCCCCTG   1755
TGGGGGCCTG TGAGGGTGAC TACGGGGGCC CACTTGCCTG CTTTACCCAC AACTGCTGGG   1815
TCCTGGAAGG AATTATAATC CCCAACCGAG TATGCGCAAG GTCCCGCTGG CCAGCTGTCT   1875
TCACGCGTGT CTCTGTGTTT GTGGACTGGA TTCACAAGGT CATGAGACTG GGTTAGGCCC   1935
AGCCTTGATG CCATATGCCT TGGGGAGGAC AAAACTTCTT GTCAGACATA AAGCCATGTT   1995
TCCTCTTTAA AAAAAAAAAA AAAAAA                                        2021
```

( 2 ) INFORMATION FOR SEQ ID NO:4:

( i ) SEQUENCE CHARACTERISTICS:
( A ) LENGTH: 2188 base pairs
( B ) TYPE: nucleic acid
( C ) STRANDEDNESS: single
( D ) TOPOLOGY: linear ( i i ) MOLECULE TYPE: cDNA to mRNA ( i v ) ANTI-SENSE: no ( v i ) ORIGINAL SOURCE:
( A ) ORGANISM: mouse
( B ) STRAIN: C57BL/6
( D ) DEVELOPMENTAL STAGE: adult
( F ) TISSUE TYPE: liver ( v i i ) IMMEDIATE SOURCE:
( A ) LIBRARY: cDNA
( B ) CLONE: ML5-2

( v i i i ) POSITION IN GENOME:
( A ) CHROMOSOME/SEGMENT: mouse 9, Hgfl locus
( B ) MAP POSITION: Trf-Gnai-2-Hgfl- Cck ( i x ) FEATURE:
( C ) IDENTIFICATION METHOD: experimental ( x ) PUBLICATION INFORMATION:
( K ) RELEVANT RESIDUES IN SEQ ID NO: 4: 1 TO 2188

( x i ) SEQUENCE DESCRIPTION: SEQ ID NO:4:

```
G GCT CTT GGG CCG CGC TCA CCA CTG AAT GAC TTC CAG CTG TTC CGG      46
  Ala Leu Gly Pro Arg Ser Pro Leu Asn Asp Phe Gln Leu Phe Arg
  20                  25                  30

GGC ACA GAG TTA AGG AAC CTG TTA CAC ACA GCG GTG CCG GGG CCA TGG    94
Gly Thr Glu Leu Arg Asn Leu Leu His Thr Ala Val Pro Gly Pro Trp
35                  40                  45

CAG GAG GAT GTG GCA GAT GCT GAG GAG TGT GCT AGG CGC TGT GGG CCC   142
Gln Glu Asp Val Ala Asp Ala Glu Glu Cys Ala Arg Arg Cys Gly Pro
50                  55                  60

CTT CTG GAC TGT CGG GCC TTC CAC TAC AAC ATG AGC AGC CAT GGT TGC   190
Leu Leu Asp Cys Arg Ala Phe His Tyr Asn Met Ser Ser His Gly Cys
65                  70                  75

CAG CTG CTG CCG TGG ACC CAG CAC TCG CTG CAC ACA CAG CTA TAC CAC   238
Gln Leu Leu Pro Trp Thr Gln His Ser Leu His Thr Gln Leu Tyr His
80                  85                  90

TCG AGT CTG TGC CAT CTC TTC CAG AAG AAA GAT TAT GTG CGG ACC TGC   286
Ser Ser Leu Cys His Leu Phe Gln Lys Lys Asp Tyr Val Arg Thr Cys
95                  100                 105                 110
```

-continued

```
ATT ATG GAC AAT GGG GTC AGC TAC CGG GGC ACT GTG GCC AGG ACA GCT     334
Ile Met Asp Asn Gly Val Ser Tyr Arg Gly Thr Val Ala Arg Thr Ala
115                 120                 125

GGT GGC CTG CCC TGC CAA GCC TGG AGT CGC AGG TTC CCC AAT GAC CAC     382
Gly Gly Leu Pro Cys Gln Ala Trp Ser Arg Arg Phe Pro Asn Asp His
130                 135                 140

AAG TAT ACG CCC ACG CCA AAG AAT GGC CTG GAA GAG AAC TTC TGT AGG     430
Lys Tyr Thr Pro Thr Pro Lys Asn Gly Leu Glu Glu Asn Phe Cys Arg
145                 150                 155

AAC CCT GAT GGG GAT CCC AGA GGT CCC TGG TGC TAC ACA ACA AAC CGC     478
Asn Pro Asp Gly Asp Pro Arg Gly Pro Trp Cys Tyr Thr Thr Asn Arg
160                 165                 170

AGT GTG CGT TTC CAG AGC TGT GGC ATC AAA ACC TGC AGG GAG GCT GTT     526
Ser Val Arg Phe Gln Ser Cys Gly Ile Lys Thr Cys Arg Glu Ala Val
175                 180                 185                 190

TGT GTT CTG TGC AAC GGT GAG GAT TAC CGT GGC GAG GTA GAC GTT ACA     574
Cys Val Leu Cys Asn Gly Glu Asp Tyr Arg Gly Glu Val Asp Val Thr
195                 200                 205

GAG TCA GGG CGG GAG TGT CAA CGC TGG GAC CTG CAG CAC CCC CAC TCG     622
Glu Ser Gly Arg Glu Cys Gln Arg Trp Asp Leu Gln His Pro His Ser
210                 215                 220

CAC CCT TTC CAG CCT GAA AAG TTC CTA GAC AAA GAT CTG AAA GAC AAC     670
His Pro Phe Gln Pro Glu Lys Phe Leu Asp Lys Asp Leu Lys Asp Asn
225                 230                 235

TAT TGT CGT AAT CCG GAC GGA TCT GAG CGG CCC TGG TGC TAC ACC ACA     718
Tyr Cys Arg Asn Pro Asp Gly Ser Glu Arg Pro Trp Cys Tyr Thr Thr
240                 245                 250

GAC CCG AAT GTT GAG CGA GAA TTC TGC GAC CTG CCC AGT TGC GGG CCT     766
Asp Pro Asn Val Glu Arg Glu Phe Cys Asp Leu Pro Ser Cys Gly Pro
255                 260                 265                 270

AAC CTG CCT CCG ACC GTC AAA GGA TCC AAG TCA CAG CGG CGC AAC AAG     814
Asn Leu Pro Pro Thr Val Lys Gly Ser Lys Ser Gln Arg Arg Asn Lys
275                 280                 285

GGC AAG GCT CTT AAC TGC TTC CGC GGA AAA GGT GAA GAC TAT CGA GGC     862
Gly Lys Ala Leu Asn Cys Phe Arg Gly Lys Gly Glu Asp Tyr Arg Gly
290                 295                 300

ACA ACC AAT ACC ACC TCT GCG GGC GTG CCC TGC CAG CGG TGG GAT GCG     910
Thr Thr Asn Thr Thr Ser Ala Gly Val Pro Cys Gln Arg Trp Asp Ala
305                 310                 315

CAG AGT CCA CAC CAG CAC CGC TTT GTG CCA GAG AAA TAT GCT TGC AAG     958
Gln Ser Pro His Gln His Arg Phe Val Pro Glu Lys Tyr Ala Cys Lys
320                 325                 330

GAC CTT CGT GAG AAT TTC TGC CGG AAT CCT GAT GGC TCC GAG GCG CCT    1006
Asp Leu Arg Glu Asn Phe Cys Arg Asn Pro Asp Gly Ser Glu Ala Pro
335                 340                 345                 350

TGG TGC TTC ACA TCT CGA CCT GGT TTG CGC ATG GCC TTC TGC CAC CAG    1054
Trp Cys Phe Thr Ser Arg Pro Gly Leu Arg Met Ala Phe Cys His Gln
355                 360                 365

ATC CCA CGC TGC ACT GAA GAA CTG GTG CCA GAG GGA TGC TAC CAC GGC    1102
Ile Pro Arg Cys Thr Glu Glu Leu Val Pro Glu Gly Cys Tyr His Gly
370                 375                 380

TCA GGT GAA CAG TAT CGT GGC TCA GTC AGC AAG ACG CGC AAG GGC GTT    1150
Ser Gly Glu Gln Tyr Arg Gly Ser Val Ser Lys Thr Arg Lys Gly Val
385                 390                 395

CAG TGC CAG CAC TGG TCC TCT GAG ACA CCG CAC AAG CCA CAA TTT ACA    1198
Gln Cys Gln His Trp Ser Ser Glu Thr Pro His Lys Pro Gln Phe Thr
400                 405                 410

CCC ACC TCG GCA CCG CAG GCG GGA CTG GAG GCC AAC TTC TGC AGG AAT    1246
Pro Thr Ser Ala Pro Gln Ala Gly Leu Glu Ala Asn Phe Cys Arg Asn
415                 420                 425                 430

CCT GAT GGG GAT AGC CAT GGG CCC TGG TGC TAT ACC TTG GAC CCG GAT    1294
Pro Asp Gly Asp Ser His Gly Pro Trp Cys Tyr Thr Leu Asp Pro Asp
```

-continued

```
435                     440                     445

ATC CTG TTT GAC TAC TGT GCC CTA CAG CGC TGT GAT GAT GAC CAG CCA      1342
Ile Leu Phe Asp Tyr Cys Ala Leu Gln Arg Cys Asp Asp Asp Gln Pro
450                     455                     460

CCA TCC ATT CTG GAC CCC CCA GAC CAG GTG GTG TTT GAA AAG TGT GGC      1390
Pro Ser Ile Leu Asp Pro Pro Asp Gln Val Val Phe Glu Lys Cys Gly
465                     470                     475

AAG AGA GTT GAC AAG AGT AAT AAA CTT CGT GTG GTG GGA GGC CAT CCT      1438
Lys Arg Val Asp Lys Ser Asn Lys Leu Arg Val Val Gly Gly His Pro
480                     485                     490

GGG AAC TCC CCA TGG ACG GTC AGC TTG CGG AAT CGA CAG GGC CAG CAT      1486
Gly Asn Ser Pro Trp Thr Val Ser Leu Arg Asn Arg Gln Gly Gln His
495                     500                     505                 510

TTC TGT GGG GGC TCC CTA GTG AAG GAG CAG TGG GTA CTG ACT GCC CGG      1534
Phe Cys Gly Gly Ser Leu Val Lys Glu Gln Trp Val Leu Thr Ala Arg
515                     520                     525

CAA TGC ATC TGG TCA TGC CAC GAA CCT CTC ACA GGA TAC GAG GTA TGG      1582
Gln Cys Ile Trp Ser Cys His Glu Pro Leu Thr Gly Tyr Glu Val Trp
530                     535                     540

TTG GGT ACA ATT AAC CAG AAC CCA CAG CCT GGA GAG GCA AAC CTG CAG      1630
Leu Gly Thr Ile Asn Gln Asn Pro Gln Pro Gly Glu Ala Asn Leu Gln
545                     550                     555

AGG GTC CCA GTG GCC AAG GCA GTG TGC GGC CCT GCA GGC TCC CAG CTT      1678
Arg Val Pro Val Ala Lys Ala Val Cys Gly Pro Ala Gly Ser Gln Leu
560                     565                     570

GTT CTG CTC AAG CTG GAG AGA CCT GTG ATC CTG AAC CAT CAC GTG GCC      1726
Val Leu Leu Lys Leu Glu Arg Pro Val Ile Leu Asn His His Val Ala
575                     580                     585                 590

CTG ATT TGC CTG CCT CCT GAA CAG TAT GTG GTA CCT CCA GGG ACC AAG      1774
Leu Ile Cys Leu Pro Pro Glu Gln Tyr Val Val Pro Pro Gly Thr Lys
595                     600                     605

TGT GAG ATC GCA GGC TGG GGT GAA TCC ATC GGT ACA AGC AAT AAC ACA      1822
Cys Glu Ile Ala Gly Trp Gly Glu Ser Ile Gly Thr Ser Asn Asn Thr
610                     615                     620

GTC CTT CAT GTG GCC TCG ATG AAT GTC ATC TCC AAC CAG GAA TGT AAC      1870
Val Leu His Val Ala Ser Met Asn Val Ile Ser Asn Gln Glu Cys Asn
625                     630                     635

ACG AAG TAC CGA GGA CAC ATA CAA GAG AGT GAG ATA TGC ACC CAG GGA      1918
Thr Lys Tyr Arg Gly His Ile Gln Glu Ser Glu Ile Cys Thr Gln Gly
640                     645                     650

CTG GTG GTC CCT GTG GGG GCT TGT GAG GGT GAC TAC GGG GGC CCA CTT      1966
Leu Val Val Pro Val Gly Ala Cys Glu Gly Asp Tyr Gly Gly Pro Leu
655                     660                     665                 670

GCC TGC TAT ACC CAT GAC TGC TGG GTC CTA CAG GGA CTT ATC ATC CCG      2014
Ala Cys Tyr Thr His Asp Cys Trp Val Leu Gln Gly Leu Ile Ile Pro
675                     680                     685

AAC AGA GTG TGT GCA CGG CCC CGC TGG CCA GCT ATC TTC ACA CGG GTG      2062
Asn Arg Val Cys Ala Arg Pro Arg Trp Pro Ala Ile Phe Thr Arg Val
690                     695                     700

TCT GTG TTC GTG GAC TGG ATT AAC AAG GTC ATG CAG CTG GAG              2104
Ser Val Phe Val Asp Trp Ile Asn Lys Val Met Gln Leu Glu
705                     710                     715

TAGGCCTGCT TTTGAGCCCT TAGAGATGTC AAGACTTCTC AAACATAAAG CGGCCTTTTC    2164

TCTCTGTCAA AAAAAAAAAA AAAA                                           2188
```

( 2 ) INFORMATION FOR SEQ ID NO:5:

( i ) SEQUENCE CHARACTERISTICS:
( A ) LENGTH: 6751 base pairs
( B ) TYPE: nucleic acid
( C ) STRANDEDNESS: single
( D ) TOPOLOGY: linear -continued ( i i ) MOLECULE TYPE: genomic DNA ( i v ) ANTI-SENSE: no ( v i ) ORIGINAL SOURCE:
( A ) ORGANISM: mouse
( B ) STRAIN: Balb/c
( D ) DEVELOPMENTAL STAGE: adult
( F ) TISSUE TYPE: liver ( v i i ) IMMEDIATE SOURCE:
( A ) LIBRARY: genomic
( B ) CLONE: MGL5-12

( v i i i ) POSITION IN GENOME:
( A ) CHROMOSOME/SEGMENT: mouse 9, Hgfl locus
( B ) MAP POSITION: Trf-Gnai-2-Hgfl- Cck ( i x ) FEATURE:
( C ) IDENTIFICATION METHOD: experimental ( x ) PUBLICATION INFORMATION:
( K ) RELEVANT RESIDUES IN SEQ ID NO: 5: 1 TO 6751

( x i ) SEQUENCE DESCRIPTION: SEQ ID NO:5:

```
AGATCTGATC GGCCAGGGGC TCGAGGGGAG TCACCGAACC CGCCCGGCTC ATAGCCAGGC    60

CGCCTCTCAC TCACCCCCGG CCTCAGCCTC CGCGACCGGC TCACAACATC CGCCCAGCTT   120

TTCGGCTACG GCACCCGTCC AGGCCAAACC GCGTGCTCGC TCGAGCGCTG CTCCAGCCGC   180

GCACGCGCAT ATGCACAGAC CGCAACAGGC TGGCAGAAAA CCCTCCTCCG TCTCCTACCA   240

AGGTGTTTAC CCGTTTTGCC TGATGGTCCA CCTGTTTCGC CCCCACCTTT CCTAGCCCAG   300

CCGTAGCAGG GACTATGTTC TAATCGGTCC CTAGGTCCAC CTGTCTTAAC TCCTACCTTG   360

CCTGGAGGAG GCCTGACCCA CATGCAGCCT GAAAGACCAC TTCTGACAGC AGATTTGCTA   420

CCTGTCACAG CCGCGCACGC CCCCTCCAGA TGGTCATTGA CACCAGATCC AATGGGCAGG   480

GTTGCTTAGC TTACCCTGGT TTGACACTTC TGAGGGGCGA TGGGATGGAT GCTCCTCGGA   540

TGTGCTGCTA GGGGTGTAGG CTGACTGCCC TACAGCTGGG ACTCAGCTGA TAAGGCAGCT   600

TGAACAGGGA GAGGCAGCAT TGGGACTGGG GAAATTGCAG TCCTCACTTT ACAAGAAGAA   660

ACTGAGGCCC AGAAAAGTAT AATCCAGGGG TCTGGGAAAT CTTGGCAACT CCTGTATAGC   720

AGAGTCTTTT GGCATAGAAG TGTCAGTGGT GATGGCAGCC ACTGTGGTCA CTAGACTCTT   780

GACATGTGAC CCGTGTAACT GAAAATTTCA GTTTTTCACT TTGTAAATCG TAATCACATA   840

GAGTCTGACT ACTGTGATGG GTACCACACC TCTACAGTAA AGCAGGCACC AGGGACTCCA   900

TGCAACTTCT GGAGCGCGTG TAGCAACAGC ATGCGACCTC AGGGATAGAT GGTGGCAGGA   960

AGACAGTGGA GTGATCTTGG CAAGTCTGGG GATTGCATAG AGTAGACGGG CTCTGCCTCA  1020

GGGACACCTA ACGTTTCCAC ACAGAACCCT CCTAAGTCCT GCCTACCACA CAGAGAGGCC  1080

TCTCAGGATC CAGCTGCAAT GAGACAGCAC TCGAGGGCCT CAAACCTAGG CTCCACCTAG  1140

CAACTGTCAC CCTATGTGTC AGTCAAGTCC AGGCAGGTTC AGAGAGGGGG TGTGGAGCCA  1200

GAGTCACCCA ATCCTGAAGG GACAGATTTC ACCATTTCCG GGATGGGGCT GTGGTGGGTC  1260

ACCGTGCAGC CTCCAGCTTA GGAGA ATG GGG TGG CTC CCA CTT CTG CTG CTT     1312
                            Met Gly Trp Leu Pro Leu Leu Leu Leu
                                                  5

CTG GTA CAG TGT TCA AGG GCT CTT G GTGAGTGTCA CCCACCCTGA TCCCAGTCTG  1367
Leu Val Gln Cys Ser Arg Ala Leu G
 10                 15

CCTTCACGAG GGAGTTCACC CCTGGTCTAC ATAGCTATTC TCATTGAGAG TTTACTTTTC  1427

TTTGGGTCCG GGATCAGTGA CCTTGGCCTG TTGAGCAGAG CTGAGAAGGC CTGGGAATTC  1487
```

-continued

```
AAATACACAC AGTCTGATCA GGACTACATT AGAGCATACT GTAGCCCAGA GGCAGTCTTT   1547

CAACCAGAGA AACTATCCAA CCCAGAAGGC AGGGCTCCTA AGCCCGATGC ACCACTGTAA   1607

CTTATGCCTT TATTCTGGTG AGAGGCCAGA CTTGGGGCCT TCCCCAGGAA GTGTCCAAGC   1667

ATTCTCATCT GAGGGGTGAG AAGGGGCAAG TGTCACAAGG CCAACACACT GTCACCCAAA   1727

TTCTCATGGA GTGGATGTGG TAGACCAGAG CCCAGTGCCA GGTCTCCTAG CAGATGGGCA   1787

ATAATCACTG TATCTGGGCC TCCCCAGCTC ACTGGCATGA AGGGACTTGC TGGGCCCTTG   1847

AAAATATACA TAAGGCCTGC CCCAAAGACC TTGTATTAGA TTCCCTAAAT GAACAAAAGA   1907

TAGGGTGTGT TAAAGTACTA ATGCGCTCAT GCTCACCACG CAG GG CAG CGC TCA      1961

ly Gln Arg Ser
20

CCA CTG AAT GAC TTC CAG CTG TTC CGG GGC ACA GAG TTA AGG AAC CTG   2009
Pro Leu Asn Asp Phe Gln Leu Phe Arg Gly Thr Glu Leu Arg Asn Leu
25                  30                  35

TTA CAC ACA GCG GTG CCG GGG CCA TGG CAG GAG GAT GTG GCA GAT GCT   2057
Leu His Thr Ala Val Pro Gly Pro Trp Gln Glu Asp Val Ala Asp Ala
40                  45                  50

GAG GAG TGT GCT AGG CGC TGT GGG CCC CTT CTG GAC TGT CG GTGAGTGGCT   2108
Glu Glu Cys Ala Arg Arg Cys Gly Pro Leu Leu Asp Cys Ar
55                  60                  65

AAGTAGCCTA GATATGGCTG AGGGCATGAG AATCTGGGTT GCCAGTTAAC TTTGTGTCTG   2168

CCACCCCCCC CCCCTTCTCC AG G GCC TTC CAC TAC AAC ATG AGC AGC CAT   2218
g Ala Phe His Tyr Asn Met Ser Ser His
70                  75

GGT TGC CAG CTG CTG CCG TGG ACC CAG CAC TCG CTG CAC ACA CAG CTA   2266
Gly Cys Gln Leu Leu Pro Trp Thr Gln His Ser Leu His Thr Gln Leu
80                  85                  90

TAC CAC TCG AGT CTG TGC CAT CTC TTC CAG AAG AAA G GCAAGTGGTG   2313
Tyr His Ser Ser Leu Cys His Leu Phe Gln Lys Lys A
95                  100

GTGAGGAGGG GAAACAGGCT GAGTAACAGG GGCCACGAGG CTCAGGCCTG TTGACCTTCC   2373

TCCATTGCTT CCAG AT TAT GTG CGG ACC TGC ATT ATG GAC AAT GGG GTC   2422
sp Tyr Val Arg Thr Cys Ile Met Asp Asn Gly Val
110                 115

AGC TAC CGG GGC ACT GTG GCC AGG ACA GCT GGT GGC CTG CCC TGC CAA   2470
Ser Tyr Arg Gly Thr Val Ala Arg Thr Ala Gly Gly Leu Pro Cys Gln
120                 125                 130

GCC TGG AGT CGC AGG TTC CCC AAT GAC CAC AA GTGAGTCAGA CACTTCAGGT   2522
Ala Trp Ser Arg Arg Phe Pro Asn Asp His Ly
135                 140

CAGACCGTTA GGCCTGAAGC AGTATTCCCC CAGTGTGCAC TGTAGTAAGA ATCTTTGTCT   2582

ACAG G TAT ACG CCC ACG CCA AAG AAT GGC CTG GAA GAG AAC TTC TGT   2629
s Tyr Thr Pro Thr Pro Lys Asn Gly Leu Glu Glu Asn Phe Cys
145                 150                 155

AGG AAC CCT GAT GGG GAT CCC AGA GGT CCC TGG TGC TAC ACA ACA AAC   2677
Arg Asn Pro Asp Gly Asp Pro Arg Gly Pro Trp Cys Tyr Thr Thr Asn
160                 165                 170

CGC AGT GTG CGT TTC CAG AGC TGT GGC ATC AAA ACC TGC AGG GAG G   2723
Arg Ser Val Arg Phe Gln Ser Cys Gly Ile Lys Thr Cys Arg Glu A
175                 180                 185

GTAAGCGGCT GGGGTCAATC AAGCCTAAGG AGGGAGTGAT AGGCCTGCCC CCACTTAGAA   2783

GTGCATTGGC CCTGTTTCCA G CT GTT TGT GTT CTG TGC AAC GGT GAG GAT   2833
la Val Cys Val Leu Cys Asn Gly Glu Asp
190                 195

TAC CGT GGC GAG GTA GAC GTT ACA GAG TCA GGG CGG GAG TGT CAA CGC   2881
Tyr Arg Gly Glu Val Asp Val Thr Glu Ser Gly Arg Glu Cys Gln Arg
200                 205                 210
```

-continued

```
TGG GAC CTG CAG CAC CCC CAC TCG CAC CCT TTC CAG CCT GAA AA          2925
Trp Asp Leu Gln His Pro His Ser His Pro Phe Gln Pro Glu Ly
215                 220                 225

GTATGTAGGC AGAATCCTTA TTTTGAGGGT GGGGCTCAGC TCTACTGGGA CTGAGTCCCA  2985

GAGTCTTGTT ACTGCTTTCA G G TTC CTA GAC AAA GAT CTG AAA GAC AAC TAT  3037
s Phe Leu Asp Lys Asp Leu Lys Asp Asn Tyr
230                 235

TGT CGT AAT CCG GAC GGA TCT GAG CGG CCC TGG TGC TAC ACC ACA GAC     3085
Cys Arg Asn Pro Asp Gly Ser Glu Arg Pro Trp Cys Tyr Thr Thr Asp
240                 245                 250                 255

CCG AAT GTT GAG CGA GAA TTC TGC GAC CTG CCC AGT TGC G GTAGGCTGCA   3135
Pro Asn Val Glu Arg Glu Phe Cys Asp Leu Pro Ser Cys G
260                 265

GGGTCAGGGT CTAGGAAGGA GCTTGGAAAA AACTGGCGGG CACGGTTCAA CTGGGAGAGG  3195

TACTAGGGAA GTTAGGCGTG GGTAGAGAGC AAAGCCTGCT GAGTACCAGA GACCAATTCC  3255

AGTTTTCGGT CAG GG CCT AAC CTG CCT CCG ACC GTC AAA GGA TCC AAG TCA  3306
ly Pro Asn Leu Pro Pro Thr Val Lys Gly Ser Lys Ser
270                 275                 280

CAG CGG CGC AAC AAG GGC AAG GCT CTT AAC TGC TTC CGC GGA AAA GGT     3354
Gln Arg Arg Asn Lys Gly Lys Ala Leu Asn Cys Phe Arg Gly Lys Gly
285                 290                 295

GAA GAC TAT CGA GGC ACA ACC AAT ACC ACC TCT GCG GGC GTG CCC TGC     3402
Glu Asp Tyr Arg Gly Thr Thr Asn Thr Thr Ser Ala Gly Val Pro Cys
300                 305                 310

CAG CGG TGG GAT GCG CAG AGT CCA CAC CAG CAC CGC TTT GTG CCA GAG     3450
Gln Arg Trp Asp Ala Gln Ser Pro His Gln His Arg Phe Val Pro Glu
315                 320                 325

AAA TAT GCT TGC AA GTGAGGTGAC AGGCCGGAGC AGGGAGAGTG CACCTGTGGG      3504
Lys Tyr Ala Cys Ly
330

TGGAGGCAGA GCGTATGCGA AGGTGGGACC TGGGGGCGGA GTCAGAGGTT CCAGCCTACT  3564

GCGGGTTGGC TGGTGGGCTA GGTGGGACCC CACTCTCGAT AAGGGAAGTG ACTACTCAG   3623

G GAC CTT CGT GAG AAT TTC TGC CGG AAT CCT GAT GGC TCC GAG GCG       3669
s Asp Leu Arg Glu Asn Phe Cys Arg Asn Pro Asp Gly Ser Glu Ala
335                 340                 345
CCT TGG TGC TTC ACA TCT CGA CCT GGT TTG CGC ATG GCC TTC TGC CAC     3717
Pro Trp Cys Phe Thr Ser Arg Pro Gly Leu Arg Met Ala Phe Cys His
350                 355                 360                 365

CAG ATC CCA CGC TGC ACT GAA GAA CTG GTG CCA GAG G GTGAGGCTGG        3764
Gln Ile Pro Arg Cys Thr Glu Glu Leu Val Pro Glu G
370                 375

AGCGGGGGTA CAGAATCTGG GCAGGAATCA ACCCAGGGCT GACCACCGCT CTTGCCTGCC  3824

CACCACAG GA TGC TAC CAC GGC TCA GGT GAA CAG TAT CGT GGC TCA GTC     3873
ly Cys Tyr His Gly Ser Gly Glu Gln Tyr Arg Gly Ser Val
380                 385                 390

AGC AAG ACG CGC AAG GGC GTT CAG TGC CAG CAC TGG TCC TCT GAG ACA     3921
Ser Lys Thr Arg Lys Gly Val Gln Cys Gln His Trp Ser Ser Glu Thr
395                 400                 405

CCG CAC AAG CCA CA GTGAGTGTGT GCTATGTGCA GATAGGGCCT TAACTCTAGG      3975
Pro His Lys Pro Gl
410

GCAGAATACC TTAAGTTCTT GTGAGCCTAA AGAGGGTCTA AGTGGCCTGA TGTGTCCCCC  4035

TACCTCCTGC CCCTACATCT AG A TTT ACA CCC ACC TCG GCA CCG CAG GCG     4085
n Phe Thr Pro Thr Ser Ala Pro Gln Ala
415                 420

GGA CTG GAG GCC AAC TTC TGC AGG AAT CCT GAT GGG GAT AGC CAT GGG     4133
Gly Leu Glu Ala Asn Phe Cys Arg Asn Pro Asp Gly Asp Ser His Gly
425                 430                 435
```

-continued

```
CCC TGG TGC TAT ACC TTG GAC CCG GAT ATC CTG TTT GAC TAC TGT GCC     4181
Pro Trp Cys Tyr Thr Leu Asp Pro Asp Ile Leu Phe Asp Tyr Cys Ala
440                 445                 450

CTA CAG CGC TGT G GTTAGTGCTT AAGACTTCCC CTTGTCTGGG TTTCAAACCT       4234
Leu Gln Arg Cys A
455

CACCTCCATA GACTGGCTCC CTTAACCTGA GTGAACTTGA TCTTGCAG AT GAT GAC     4290
sp Asp Asp
460

CAG CCA CCA TCC ATT CTG GAC CCC CCA G GTATGGGGTT GGGCCAATTG         4338
Gln Pro Pro Ser Ile Leu Asp Pro Pro A
465

TGGGTACACA GTCTTTGACC CTGACCCTCA CTGAAGGTTT CATCCTGCCC CATCCCCAG    4397

AC CAG GTG GTG TTT GAA AAG TGT GGC AAG AGA GTT GAC AAG AGT AAT      4444
sp Gln Val Val Phe Glu Lys Cys Gly Lys Arg Val Asp Lys Ser Asn
475                 480                 485

AAA CTT CGT GTG GTG GGA GGC CAT CCT GGG AAC TCC CCA TGG ACG GTC     4492
Lys Leu Arg Val Val Gly Gly His Pro Gly Asn Ser Pro Trp Thr Val
490                 495                 500

AGC TTG CGG AAT CG GTGAGGCCTA AGCGCTTATC TCAAGGAGTG GAGGCTGGAA      4546
Ser Leu Arg Asn Ar
505

ACTCTGTGGC TTTATCAGTA GAAGATGGAT GCCTGGCCTT GTACCAAAAG GTCCTTGTCA   4606

GAAATGACAG TCTAGCATGT GTCCCAGGAC TCAGTGTGGC TTCTCATCTT TACTCCTCTA   4666

G A CAG GGC CAG CAT TTC TGT GGG GGC TCC CTA GTG AAG GAG CAG TGG     4713
g Gln Gly Gln His Phe Cys Gly Gly Ser Leu Val Lys Glu Gln Trp
510                 515                 520

GTA CTG ACT GCC CGG CAA TGC ATC TGG TCA TG GTGAGCAGAC TGGGGACTCC    4765
Val Leu Thr Ala Arg Gln Cys Ile Trp Ser Cy
525                 530

TAGCCTACCT CTCCCTGCCA TTGTCTGTCC CACAAGCAAA CTAAATTGTG ACAGCTGATT   4825

GGGAGTCAAG CATGAACTAG CAGAGTCTCT TTCTCCCAG C CAC GAA CCT CTC ACA    4880
s His Glu Pro Leu Thr
535

GGA TAC GAG GTA TGG TTG GGT ACA ATT AAC CAG AAC CCA CAG CCT GGA     4928
Gly Tyr Glu Val Trp Leu Gly Thr Ile Asn Gln Asn Pro Gln Pro Gly
540                 545                 550

GAG GCA AAC CTG CAG AGG GTC CCA GTG GCC AAG GCA GTG TGC GGC CCT     4976
Glu Ala Asn Leu Gln Arg Val Pro Val Ala Lys Ala Val Cys Gly Pro
555                 560                 565

GCA GGC TCC CAG CTT GTT CTG CTC AAG CTG GAG AG GTATGTGGAT           5021
Ala Gly Ser Gln Leu Val Leu Leu Lys Leu Glu Ar
570                 575                 580

GTGTTGAGAG GGTGTGAGGC AGGGCTAGCC TCATGGTCAT AGGTCCTGAA AACCCTCATT   5081
CCCACTAAAG A CCT GTG ATC CTG AAC CAT CAC GTG GCC CTG ATT TGC CTG    5131
g Pro Val Ile Leu Asn His His Val Ala Leu Ile Cys Leu
585                 590

CCT CCT GAA CAG TAT GTG GTA CCT CCA GGG ACC AAG TGT GAG ATC GCA     5179
Pro Pro Glu Gln Tyr Val Val Pro Pro Gly Thr Lys Cys Glu Ile Ala
595                 600                 605                 610

GGC TGG GGT GAA TCC ATC G GTAAGAGCAC AGTGCATAGA CATGGACTGC          5228
Gly Trp Gly Glu Ser Ile G
615

TATGGGCCGG GAGGTCCAGC ACTGGTTTTG GCTCAAGGGT CCCCTCCTTA TCATTGTCTG   5288

TACTTCAG GT ACA AGC AAT AAC ACA GTC CTT CAT GTG GCC TCG ATG AAT     5337
ly Thr Ser Asn Asn Thr Val Leu His Val Ala Ser Met Asn
620                 625                 630

GTC ATC TCC AAC CAG GAA TGT AAC ACG AAG TAC CGA GGA CAC ATA CAA     5385
Val Ile Ser Asn Gln Glu Cys Asn Thr Lys Tyr Arg Gly His Ile Gln
635                 640                 645
```

-continued

```
GAG AGT GAG ATA TGC ACC CAG GGA CTG GTG GTC CCT GTG GGG GCT TGT    5433
Glu Ser Glu Ile Cys Thr Gln Gly Leu Val Val Pro Val Gly Ala Cys
650                 655                 660

GAG GTCAGTGGGA GAGCCCCTGG GCCAGCCTGG GAAGGGCTTG GGAGCTGAAA         5486
Glu

TTATAGTACT TGATTGCCAA GGGGGTGGGA TGTCAGGAGA GGGTAGTCAC TGCCGAGGTC  5546

CAGAGCCTTC ACCCGTTTTT CTACCTGCCA G GGT GAC TAC GGG GGC CCA CTT     5598
                                   Gly Asp Tyr Gly Gly Pro Leu
                                   665                 670

GCC TGC TAT ACC CAT GAC TGC TGG GTC CTA CAG GGA CTT ATC ATC CCG    5646
Ala Cys Tyr Thr His Asp Cys Trp Val Leu Gln Gly Leu Ile Ile Pro
675                 680                 685

AAC AGA GTG TGT GCA CGG CCC CGC TGG CCA GCT ATC TTC ACA CGG GTG    5694
Asn Arg Val Cys Ala Arg Pro Arg Trp Pro Ala Ile Phe Thr Arg Val
690                 695                 700

TCT GTG TTC GTG GAC TGG ATT AAC AAG GTC ATG CAG CTG GAG            5736
Ser Val Phe Val Asp Trp Ile Asn Lys Val Met Gln Leu Glu
705                 710                 715

TAGGCCTGCT TTTGAGCCCT TAGAGATGTC AAGACTTCTC AAACATAAAG CGGCCTTTTC  5796

TCTCTGTCTG TATAGAGTGC TTCTTAGTTTCTGT CTCTAGGGAA GGTGTTGACT CCTTGC  5856

AAGAGGCTGT GTGGCTTAAG ACCAGCACAC TCTAGGCTAA GTGCTCTGAT CCCAGAACAA  5916

CTTCAAAAGG TATGTACTGT GTGTGGGCAG GGTGCACCAT CTTCCAGAGG CACTCCTGGG  5976

AATGCAAGGA CAGTGCAGAA GTTCCCAGCC CATGGACCAG AGCAGAAAGA GTGATGTAGG  6036

TCTACACCAG TCCCGTTTGG CTAGGACAGG CAGGGGTTGA GTCTCTCATG GCTTCTCTCT  6096

GTCACATGAC AGGGATGAAT ACACTGTGGA TATCAAACCA AGGACCTAGG GTTTCTGAAC  6156

CCCAAGGTAG AGGCTGGGGC TGGGGATGGC TTGTACAAAG TACCAGCACA GACCAGGCTC  6216

TGTGTCCTCC TTTATTATGA TTAGAGTCCA TAGTCCTCTG CCCACTCATT CGGAGTCCAG  6276

AGCCCAGGAA ACCTCTAGGC AGTTCTGCCA GATCCTGGGG CTTACCGAAG AGCAAAGTTC  6336

GAGACGGACT GCCCAGCTCA CAAAGAGCAA CAGGGCTTCA GCTGCCCAAG TGTGTGTGTA  6396

GCCAAAGCAC AGTGTTCATG AAGCTGTCTG ATTCCACCTC CACCTCTGAC AGCGCATGGG  6456

TGCTCTTGGG ATACAGCAGG AGCCTGTATG AGCAGCAACA CATGACATTG GAGGGTCCTG  6516

TCCTGTTTAC CTGCCACCAG CTGCCCAACT ATCCTGTACA CTCACCGGAC AGGCACATTC  6576

CGGGCCTTGA GGGCATGGTA ATACTCCAGA CCCTGCTTGA AGGGTACACG CCGGTCCTCC  6636

TGGCCCAGCA TCAGTAACAC TGGTGTCTTT ACCTAGGTGT ATGGGAGGCA AGGAGCTGTG  6696

GCGAGCTGAG CTCTGGACTC TGGAGGAATG GGTGGCACAA GGATACCTGG GTACC       6751
```

(2) INFORMATION FOR SEQ ID NO:6:

(i) SEQUENCE CHARACTERISTICS:
- (A) LENGTH: 6100 base pairs
- (B) TYPE: nucleic acid
- (C) STRANDEDNESS: single
- (D) TOPOLOGY: linear (ii) MOLECULE TYPE: genomic DNA (iv) ANTI-SENSE: no (vi) ORIGINAL SOURCE:
- (A) ORGANISM: human
- (D) DEVELOPMENTAL STAGE: fetal
- (F) TISSUE TYPE: liver (vii) IMMEDIATE SOURCE:
- (A) LIBRARY: genomic
- (B) CLONE: L5/3

-continued ( v i i i ) POSITION IN GENOME:
( A ) CHROMOSOME/SEGMENT: human 3p21/D3F15S2

( i x ) FEATURE:
( C ) IDENTIFICATION METHOD: experimental
( D ) OTHER INFORMATION: This is the combined sequence of the e from two different recombinant phage isolates (L5 & L5/3)

( x ) PUBLICATION INFORMATION:
( K ) RELEVANT RESIDUES IN SEQ ID NO:6: FROM 1 TO 6100

( x i ) SEQUENCE DESCRIPTION: SEQ ID NO:6:

CTGCAGAGGG GTTTCACCCC AACCCCAGGG CACCTCAAGT GTCCCCACCA AACCTTCCTA 60

ACACCTGTCC ACTAAGCTGT ACTAGGCCCT TGCAACTGAC CTATGGGACC CTGAGGCCTG 120

GCCCCTCATG GCTCCTGTCA CCAGGTCTCA GGTCAGGGTC CAGCAGGGCC CTGAGCTGAC 180

GTGTGGAGCC AGAGCCACCC AATCCCGTAG ACAGGTTTCA CAACTTCCCG GATGGGGCTG 240

TGGTGGGTCA CAGTGCAGCC TCCAGCCAGA AGG ATG GGG TGG CTC CCA CTC CTG 294
Met Gly Trp Leu Pro Leu Leu
5

CTG CTT CTG ACT CAA TGC TTA GGG GTC CCT G GTAAGTGCCC CCAACCCTGA 345
Leu Leu Leu Thr Gln Cys Leu Gly Val Pro G
10 15

TCCCCATCTG CCTTCAGGAG GGGGTTGGCC CCATTCTCCT ATTCTAGGAT GAGAAAAAAG 405

TCGGGAGCAG AGGCTCAGTG GGCATGGGGC AGTGACCTTG CCCTCTTGAG CACAGCTGGG 465

AAGCCCTAGG AACACATAGA CATTGCCCAC TTAGGCCTCT ATTAGCACGT CTGCTCTAGC 525

ACTGAAGCAG TGTCAGGACC ACACAGATGC ACGCACACAG CAGGCAGTGA CCCCTCCTGA 585

GCCTGATCTA CCCCTCTAAC CTAGCATATG CCTTTGTGCA GGTGAGAGCC CAGATTTGGA 645

GTCTGAATGC CTAGCCAGGG CCCTTGGCTG GGTAATGTGA TGGCTCTGAG CCTTAGCATT 705

CTCATTTGAG AGATGAGGTG GGGCAAGCTT CATCACCCAC TGCTCTCACA GAGCGTATGT 765

GTTAGATCTG AGCCCGGTGC CTGGGCCACT AAACAGAGGC ACCGGTGATA ACTACCAAGT 825

CTGGGCCTGC TTCCCAGGGG AAATTTTTTT CACAAGTATC TGTGCAGGGG GCTAGACTGG 885

CCCTTGAAAG TGCATACAGG GTCCATCCCA GAAGCTTGTA GCTTTGATCC CCTGAATGAA 945

CAAAGTGTGG ACATGCCAAT ACACATTACT GACATGTATG CCCACCTGAC CTGCACCCAC 1005

TCATGCCTAC TCTGCAG GG CAG CGC TCG CCA TTG AAT GAC TTC CAA GTG CTC 1057
ly Gln Arg Ser Pro Leu Asn Asp Phe Gln Val Leu
20 25

CGG GGC ACA GAG CTA CAG CAC CTG CTA CAT GCG GTG GTG CCC GGG CCT 1105
Arg Gly Thr Glu Leu Gln His Leu Leu His Ala Val Val Pro Gly Pro
30 35 40 45

TGG CAG GAG GAT GTG GCA GAT GCT GAA GAG TGT GCT GGT CGC TGT GGG 1153
Trp Gln Glu Asp Val Ala Asp Ala Glu Glu Cys Ala Gly Arg Cys Gly
50 55 60

CCC TTA ATG GAC TGC CG GTGAGTGGCC ACTGGGCTAG ATAAGACTGG 1200
Pro Leu Met Asp Cys Ar
65

GGGCAGGGAA GCCTGGGCTG TGGCGTTACC CTGTGCCTTC TTCTCTCCAG G GCC TTC 1257
g Ala Phe

CAC TAC AAC GTG AGC AGC CAT GGT TGC CAA CTG CTG CCA TGG ACT CAA 1305
His Tyr Asn Val Ser Ser His Gly Cys Gln Leu Leu Pro Trp Thr Gln
70 75 80 85

CAC TCG CCC CAC ACG AGG CTG CGG CGT TCT GGG CGC TGT GAC CTC TTC 1353
His Ser Pro His Thr Arg Leu Arg Arg Ser Gly Arg Cys Asp Leu Phe
90 95 100

CAG AAG AAA G GCAAGTGGGG GTGGAGAGGG GCAGGGTGGG AGACAGGGGA 1403
Gln Lys Lys A

CCTCAGCCCA AGTTGATCTT CTGTCTCTTG CTCCCAG AC TAC GTA CGG ACC TGC 1457

-continued

```
sp Tyr Val Arg Thr Cys
110

ATC ATG AAC AAT GGG GTT GGG TAC CGG GGC ACC ATG GCC ACG ACC GTG      1505
Ile Met Asn Asn Gly Val Gly Tyr Arg Gly Thr Met Ala Thr Thr Val
115                 120                 125

GGT GGC CTG CCC TGC CAG GCT TGG AGC CAC AAG TTC CCG AAT GAT CAC      1553
Gly Gly Leu Pro Cys Gln Ala Trp Ser His Lys Phe Pro Asn Asp His
130                 135                 140

AA GTGAGACAAA CACCTTCCCT CCGTCCCGGC CTGGGGCTTC CCCCAGCACA            1605
Ly

CACTATAGTG ATGCTCTGGG CCCTCAG G TAC ACG CCC ACT CTC CGG AAT GGC      1657
s Tyr Thr Pro Thr Leu Arg Asn Gly
145                 150

CTG GAA GAG AAC TTC TGC CGT AAC CCT GAT GGC GAC CCC GGA GGT CCT      1705
Leu Glu Glu Asn Phe Cys Arg Asn Pro Asp Gly Asp Pro Gly Gly Pro
155                 160                 165

TGG TGC TAC ACA ACA GAC CCT GCT GTG CGC TTC CAG AGC TGC GGC ATC      1753
Trp Cys Tyr Thr Thr Asp Pro Ala Val Arg Phe Gln Ser Cys Gly Ile
170                 175                 180

AAA TCC TGC CGG GAG G GTAAGCGGCG CCGGGTCAAG CTGGGAGAGT GGAGACAAGC    1809
Lys Ser Cys Arg Glu A
185

CCACGTCCAT CCACGAACCC ACTGGCTCTT TGTCTCCAG CC GCG TGT GTC TGG TGC    1865
la Ala Cys Val Trp Cys
190

AAT GGC GAG GAA TAC CGC GGC GCG GTA GAC CGC ACG GAG TCA GGG CGC      1913
Asn Gly Glu Glu Tyr Arg Gly Ala Val Asp Arg Thr Glu Ser Gly Arg
195                 200                 205                 210

GAG TGC CAG CGC TGG GAT CTT CAG CAC CCG CAC CAG CAC CCC TTC GAG      1961
Glu Cys Gln Arg Trp Asp Leu Gln His Pro His Gln His Pro Phe Glu
215                 220                 225

CCG GGC AA GTACGCGTAG GCGGTATCGG CGTCCTGGGG GCCGGGCTAG GGAAGGTCCA    2019
Pro Gly Ly

GGACTCCAGG GGCAGGGCTC CGTGTAGGGC AATTGGGCGG GGCCAGATAA GCCAGAGTCC    2079

CAGGGTCTTG TTCACGCCCC ATTACCGCCC CCAG G TTC CTC GAC CAA GGT CTG      2132
s Phe Leu Asp Gln Gly Leu
230                 235

GAC GAC AAC TAT TGC CGG AAT CCT GAC GGC TCC GAG CGG CCA TGG TGC      2180
Asp Asp Asn Tyr Cys Arg Asn Pro Asp Gly Ser Glu Arg Pro Trp Cys
240                 245                 250

TAC ACT ACG GAT CCG CAG ATC GAG CGA GAG TTC TGT GAC CTC CCC CGC      2228
Tyr Thr Thr Asp Pro Gln Ile Glu Arg Glu Phe Cys Asp Leu Pro Arg
255                 260                 265

TGC G GTAGGCGGCG GGGACCAGGC CTGGGAGGGT ACCTGGGAAC CTTGGGGAGG         2282
Cys G

GGCGTGGCTT GGCCGGGGAG GTAAGAGGGG CTGGGCGTGA CCTGAGAGCA TACCCCGTGG    2342

AGTACCGTAC ACCTGGGAAA GGCGGGTTTG GTCCCAGCCC CAGAGGGATC TCAGCTCTCG    2402

CTCGGGGCCC GACCTATCTC GGTCCATCTA AG GG TCC GAG GCA CAG CCC CGC       2454
ly Ser Glu Ala Gln Pro Arg
270                 275

CAA GAG GCC ACA ACT GTC AGC TGC TTC CGC GGG AAG GGT GAG GGC TAC      2502
Gln Glu Ala Thr Thr Val Ser Cys Phe Arg Gly Lys Gly Glu Gly Tyr
280                 285                 290

CGG GGC ACA GCC AAT ACC ACC ACT GCG GGC GTA CCT TGC CAG CGT TGG      2550
Arg Gly Thr Ala Asn Thr Thr Thr Ala Gly Val Pro Cys Gln Arg Trp
295                 300                 305

GAC GCG CAA ATC CCT CAT CAG CAC CGA TTT ACG CCA GAA AAA TAC GCG      2598
Asp Ala Gln Ile Pro His Gln His Arg Phe Thr Pro Glu Lys Tyr Ala
310                 315                 320
```

-continued

TGC AA GTGAGGTGGG GGGGGGGGGC GGGCGTTGGG ACGTGCTGCT GCGGGTGAGA 2653
Cys Ly

CGGGAGGAAG GTAGTCACGG GCTCAAGGCT GGAGGCTGGC GGGCTAGGGC TGAGTGGAGC 2713

GCCTGCTTAG A GAC CTT CGG GAG AAC TTC TGC CGG AAC CCC GAC GGC TCA 2763
s Asp Leu Arg Glu Asn Phe Cys Arg Asn Pro Asp Gly Ser
330 335

GAG GCG CCC TGG TGC TTC ACA CTG CGG CCC GGC ATG CGC GCG GCC TTT 2811
Glu Ala Pro Trp Cys Phe Thr Leu Arg Pro Gly Met Arg Ala Ala Phe
340 345 350

TGC TAC CAG ATC CGG CGT TGT ACA GAC GAC GTG CGG CCC CAG G 2854
Cys Tyr Gln Ile Arg Arg Cys Thr Asp Asp Val Arg Pro Gln A
355 360 365

GTGAGGCCCA AGCTTGGGGG CTACAGAGCC GGGCTGGAAG CTGGAACCGG AGGCCGGGGC 2914

GAGGTCTCGG CCTGATGGCT GCCCGCACCC GCCACAG AC TGC TAC CAC GGC GCA 2968
sp Cys Tyr His Gly Ala
370

GGG GAG CAG TAC CGC GGC ACG GTC AGC AAG ACC CGC AAG GGT GTC CAG 3016
Gly Glu Gln Tyr Arg Gly Thr Val Ser Lys Thr Arg Lys Gly Val Gln
375 380 385 390

TGC CAG CGC TGG TCC GCT GAG ACG CCG CAC AAG CCG CA GTGAGTCCCT 3064
Cys Gln Arg Trp Ser Ala Glu Thr Pro His Lys Pro Gl
395 400

GGTGCTCCCG GCCCCGCCAG GGCCCTAACC CTGGGGCGGC ATGCTTTGGT GTCTGGGACC 3124

AGAGCCTGGA AATGGTTGAG ACTACCCTGC CACGATTTTG CTCCCGCTTC CGCCTAG G 3182
n

TTC ACG TTT ACC TCC GAA CCG CAT GCA CAA CTG GAG GAG AAC TTC TGC 3230
Phe Thr Phe Thr Ser Glu Pro His Ala Gln Leu Glu Glu Asn Phe Cys
405 410 415

CGG AAC CCA GAT GGG GAT AGC CAT GGG CCC TGG TGC TAC ACG ATG GAC 3278
Arg Asn Pro Asp Gly Asp Ser His Gly Pro Trp Cys Tyr Thr Met Asp
420 425 430 435

CCA AGG ACC CCA TTC GAC TAC TGT GCC CTG CGA CGC TGC G GTGAGCACTA 3328
Pro Arg Thr Pro Phe Asp Tyr Cys Ala Leu Arg Arg Cys A
440 445

GTGACGCTTC CCCCATGACC CTGCCTCAGC CCCCACCCAA AGGCTGGCTC CCTTAACCCC 3388

AGTGAACTTT GTCTTTCAG CT GAT GAC CAG CCG CCA TCA ATC CTG GAC CCC 3439
la Asp Asp Gln Pro Pro Ser Ile Leu Asp Pro
450 455

CCA G GTTAGGAGTT GGGCCAGTTA TGGGTCAGGC CCTTTAGCCC ACGACATCCA 3493
Pro A

CACAGTCTGG GTTTCATCCA GCCCACCCCA TCCTACAG AC CAG GTG CAG TTT GAG 3548
sp Gln Val Gln Phe Glu
465

AAG TGT GGC AAG AGG GTG GAT CGG CTG GAT CAG CGG CGT TCC AAG CTG 3596
Lys Cys Gly Lys Arg Val Asp Arg Leu Asp Gln Arg Arg Ser Lys Leu
470 475 480

CGC GTG GTT GGG GGC CAT CCG GGC AAC TCA CCC TGG ACA GTC AGC TTG 3644
Arg Val Val Gly Gly His Pro Gly Asn Ser Pro Trp Thr Val Ser Leu
485 490 495

CGG AAT CG GTGAGGCACA ACTGCCTGTC TCCCACAGAG AGGAGCTGAG GTTGTGTCCT 3702
Arg Asn Ar
500

CTGTGGTTAT CCACTGGGGC TGGGAATCTA TCCGTGCCCC TTGAGAGGTC CTAGCCAAGA 3762

AGATGGCAGG TCTTACGAAT CTGTCCCAGG AGTCTGTTAC CTGTCCTAAT TCCCCACTCC 3822

TCTAG G CAG GGC CAG CAT TTC TGC GGG GGG TCT CTA GTG AAG GAG CAG 3870
g Gln Gly Gln His Phe Cys Gly Gly Ser Leu Val Lys Glu Gln
505 510 515

TGG ATA CTG ACT GCC CGG CAG TGC TTC TCC TCC TG GTGAGCCTCC 3915

-continued

```
Trp Ile Leu Thr Ala Arg Gln Cys Phe Ser Ser Cy
520                 525

CTTGTGTTTG GGGACCCAGT CTCATCCCAC CTTCCCCCTT CCCCAGGCAA GCTAACAAGT   3975

GAGCCTTGGG GCAATGGACT GAGAGTCACA AATGACCTAG CAGAGCTTCT CTCCCAG C    4033
s

CAT ATG CCT CTC ACG GGC TAT GAG GTA TGG TTG GGC ACC CTG TTC CAG     4081
His Met Pro Leu Thr Gly Tyr Glu Val Trp Leu Gly Thr Leu Phe Gln
530                 535                 540

AAC CCA CAG CAT GGA GAG CCA AGC CTA CAG CGG GTC CCA GTA GCC AAG     4129
Asn Pro Gln His Gly Glu Pro Ser Leu Gln Arg Val Pro Val Ala Lys
545                 550                 555

ATG GTG TGT GGG CCC TCA GGC TCC CAG CTT GTC CTG CTC AAG CTG GAG     4177
Met Val Cys Gly Pro Ser Gly Ser Gln Leu Val Leu Leu Lys Leu Glu
560                 565                 570                 575

AG GTATGTGGAC AACCTGGGAG GGTGTGAGGT GGGGCTGGGC CTTGTGGCCT           4229
Ar

CAGACCCTGA GTGCCCCCAT TCTTGCTAAA G A TCT GTG ACC CTG AAC CAG CGT    4282
g Ser Val Thr Leu Asn Gln Arg
580

GTG GCC CTG ATC TGC CTG CCC CCT GAA TGG TAT GTG GTG CCT CCA GGG     4330
Val Ala Leu Ile Cys Leu Pro Pro Glu Trp Tyr Val Val Pro Pro Gly
585                 590                 595

ACC AAG TGT GAG ATT GCA GGC TGG GGT GAG ACC AAA G GTAAGAGCAC        4377
Thr Lys Cys Glu Ile Ala Gly Trp Gly Glu Thr Lys G
600                 605                 610

AGTGCACAGG ACTGCTGGTG GCCAGGAGGC CAGCCCTGGA TCTTCCTGCA GGACCCTCTC   4437

CCTCTCCCCA TTCCCCTCAC TGCAG GT ACG GGT AAT GAC ACA GTC CTA AAT      4488
ly Thr Gly Asn Asp Thr Val Leu Asn
615                 620

GTG GCC TTG CTG AAT GTC ATC TCC AAC CAG GAG TGT AAC ATC AAG CAC     4536
Val Ala Leu Leu Asn Val Ile Ser Asn Gln Glu Cys Asn Ile Lys His
625                 630                 635

CGA GGA CGT GTG CGG GAG AGT GAG ATG TGC ACT GAG GGA CTG TTG GCC     4584
Arg Gly Arg Val Arg Glu Ser Glu Met Cys Thr Glu Gly Leu Leu Ala
640                 645                 650

CCT GTG GGG GCC TGT GAG GTTGGTGGCA GGGCCTGGGC AGCCCTGGAA            4632
Pro Val Gly Ala Cys Glu
655

GTATGGGGGG CTAGAAATGA ACTATTTTAT CATGAAGCAG GCTAGTCATT GCTGTGGCCC   4692

GGGGCCTCAT CAGTTCTCCT ACCTGCCAG GGT GAC TAC GGG GGC CCA CTT GCC     4745
Gly Asp Tyr Gly Gly Pro Leu Ala
660                 665

TGC TTT ACC CAC AAC TGC TGG GTC CTG GAA GGA ATT ATA ATC CCC AAC     4793
Cys Phe Thr His Asn Cys Trp Val Leu Glu Gly Ile Ile Ile Pro Asn
670                 675                 680

CGA GTA TGC GCA AGG TCC CGC TGG CCA GCT GTC TTC ACG CGT GTC TCT     4841
Arg Val Cys Ala Arg Ser Arg Trp Pro Ala Val Phe Thr Arg Val Ser
685                 690                 695

GTG TTT GTG GAC TGG ATT CAC AAG GTC ATG AGA CTG GGT TAGGCCCAGC      4890
Val Phe Val Asp Trp Ile His Lys Val Met Arg Leu Gly
700                 705                 710

CTTGATGCCA TATGCCTTGG GGAGGACAAA ACTTCTTGTC AGACATAAAG CCATGTTTCC   4950

TCTTTATGCC TGTACAGATG CTTCTTAGCC TTTGCTTCCA GGAAATGTGT CAGTGACTCC   5010

TTGCTAGGGC TCGGGTGGCT TGAGCCCAGC ACACCCTGGG CTAGGTGATC TGTCCAGCCT   5070

AGGGGCTTCC CCAACCAAGG CAATGTCCCT GGGACTACTT TTGCCCATGG GTGCCGTGGA   5130

AAGACAGGGC CTCACACTAG TCCTCCAGAC ATACTCTTGG GAAGGGTGGT ACAGAGTAGT   5190

TGCTAATGGA AGGGGCTGCA GCAGGGAAGC TAGGCTGGTA CAGAGTCCTG GTTGCCAGGA   5250
```

-continued

CAGGCAGAGG CTAAGCCTCT CACTGTTCCC TCCCTTCTCA CACTGGAGGC AGATGAAGCC 5310

CTTGTGGCTG CCACACCCAG AACCTAGGGT CTCTGCACCC CAGAGTGGGA GGTGGGGTTG 5370

GGGATGGTTT GGTACAAAGT ACCAGCAGGA ACCAGGCTCT GTGTCCTAAT TTATTATGAC 5430

TACATAGCCC ACATTCCTCT GCCCATGCAT CCGTGGAGTC CAGAGCCCAG AAAGCCTCCT 5490

GCTGCCCTGC CAGACCGTTG AGCTCCTCAA GAGGAAGTGT GGCACAGGCT GATCAGCTCA 5550

TGCAGAATGG CAGGGCTTCA GCTGCCCAAG TGTGTGCGTA GCCAGAGCAC AGCATTCATG 5610

AAGCTGTCTG ACTCCACCTC CACCTCTGAT AATGCGTGGG TGCTTTTGGG ATAGAGCAGG 5670

AGCCTGTAGG GATTAGTCAG CAACATTTAA GGTTGGAGGG TCCTCCTGTG CTCACCTGCC 5730

CACCAGCTGC CAGGGCCTTC ATGCTGCACT CACCGAACAG GCACATTCCG GGTCTTGAGG 5790

GCACGGTAAT ACTCCATGCC CTGCTTGAAG GGCACACGCC GGTCCTCCTG GCCCAACATC 5850

AGTAACAGTG GTGTCTTCAC CTGGGTGTTT GGGGAAGAGT GGGGAGCTGT GTTGAGCTGG 5910

GCCCTGGATT CTGGATGGAT GGGCAGCACA CAGGGCAAGC AGGGGGCTGC ATACCTGAGG 5970

GATGTATCTG ATGGGCGATT TGTCCAGCAT CTCAGCCCAC ACGCTGAGGT CTGGCAGGCA 6030

GTCACTGCTG AAAGGAAAGC CAGCCTCCAC CACGCACCTG CAAGACACCG AGCTGTTGCA 6090

GCCCCAGGAA 6100

( 2 ) INFORMATION FOR SEQ ID NO:7:

( i ) SEQUENCE CHARACTERISTICS:
( A ) LENGTH: 2262 base pairs
( B ) TYPE: nucleic acid
( C ) STRANDEDNESS: single
( D ) TOPOLOGY: linear ( i i ) MOLECULE TYPE: cDNA to mRNA
( A ) DESCRIPTION: Identical to sequence ID NO: 1: with 5'and adaptors added to make a full-length cDNA ( i v ) ANTI-SENSE: no ( v i ) ORIGINAL SOURCE:
( A ) ORGANISM: human
( D ) DEVELOPMENTAL STAGE: fetal
( F ) TISSUE TYPE: liver ( v i i ) IMMEDIATE SOURCE:
( A ) LIBRARY: cDNA
( B ) CLONE: #icrosoft Corp ( x ) PUBLICATION INFORMATION:
( K ) RELEVANT RESIDUES IN SEQ ID NO: 7: FROM 1 TO 2262

( x i ) SEQUENCE DESCRIPTION: SEQ ID NO:7:

```
AATTCCACC ATG GGG TGG CTC CCA AAT TCC GTC CTG CTG CTT CTG ACT      48
          Met Gly Trp Leu Pro Asn Ser Val Leu Leu Leu Leu Thr
          5                   10

CAA TAC TTA GGG GTC CCT GGG CAG CGC TCG CCA TTG AAT GAC TTC CAA    96
Gln Tyr Leu Gly Val Pro Gly Gln Arg Ser Pro Leu Asn Asp Phe Gln
15                  20                  25

GTG CTC CGG GGC ACA GAG CTA CAG CAC CTG CTA CAT GCG GTG GTG CCC   144
Val Leu Arg Gly Thr Glu Leu Gln His Leu Leu His Ala Val Val Pro
30                  35                  40                  45

GGG CCT TGG CAG GAG GAT GTG GCA GAT GCT GAA GAG TGT GCT GGT CGC   192
Gly Pro Trp Gln Glu Asp Val Ala Asp Ala Glu Glu Cys Ala Gly Arg
50                  55                  60

TGT GGG CCC TTA ATG GAC TGC CGG GCC TTC CAC TAC AAC GTG AGC AGC   240
Cys Gly Pro Leu Met Asp Cys Arg Ala Phe His Tyr Asn Val Ser Ser
65                  70                  75

CAT GGT TGC CAA CTG CTG CCA TGG ACT CAA CAC TCG CCC CAC ACG AGG   288
His Gly Cys Gln Leu Leu Pro Trp Thr Gln His Ser Pro His Thr Arg
```

-continued 80 85 90

CTG CGG CGT TCT GGG CGC TGT GAC CTC TTC CAG AAG AAA GAC TAC GTA 336
Leu Arg Arg Ser Gly Arg Cys Asp Leu Phe Gln Lys Lys Asp Tyr Val
95 100 105

CGG ACC TGC ATC ATG AAC AAT GGG GTT GGG TAC CGG GGC ACC ATG GCC 384
Arg Thr Cys Ile Met Asn Asn Gly Val Gly Tyr Arg Gly Thr Met Ala
110 115 120 125

ACG ACC GTG GGT GGC CTG CCC TGC CAG GCT TGG AGC CAC AAG TTC CCG 432
Thr Thr Val Gly Gly Leu Pro Cys Gln Ala Trp Ser His Lys Phe Pro
130 135 140

AAT GAT CAC AAG TAC ACG CCC ACT CTC CGG AAT GGC CTG GAA GAG AAC 480
Asn Asp His Lys Tyr Thr Pro Thr Leu Arg Asn Gly Leu Glu Glu Asn
145 150 155

TTC TGC CGT AAC CCT GAT GGC GAC CCC GGA GGT CCT TGG TGC TAC ACA 528
Phe Cys Arg Asn Pro Asp Gly Asp Pro Gly Gly Pro Trp Cys Tyr Thr
160 165 170

ACA GAC CCT GCT GTG CGC TTC CAG AGC TGC GGC ATC AAA TCC TGC CGG 576
Thr Asp Pro Ala Val Arg Phe Gln Ser Cys Gly Ile Lys Ser Cys Arg
175 180 185

GAG GCC GCG TGT GTC TGG TGC AAT GGC GAG GAA TAC CGC GGC GCG GTA 624
Glu Ala Ala Cys Val Trp Cys Asn Gly Glu Glu Tyr Arg Gly Ala Val
190 195 200 205

GAC CGC ACG GAG TCA GGG CGC GAG TGC CAG CGC TGG GAT CTT CAG CAC 672
Asp Arg Thr Glu Ser Gly Arg Glu Cys Gln Arg Trp Asp Leu Gln His
210 215 220

CCG CAC CAG CAC CCC TTC GAG CCG GGC AAG TTC CTC GAC CAA GGT CTG 720
Pro His Gln His Pro Phe Glu Pro Gly Lys Phe Leu Asp Gln Gly Leu
225 230 235

GAC GAC AAC TAT TGC CGG AAT CCT GAC GGC TCC GAG CGG CCA TGG TGC 768
Asp Asp Asn Tyr Cys Arg Asn Pro Asp Gly Ser Glu Arg Pro Trp Cys
240 245 250

TAC ACT ACG GAT CCG CAG ATC GAG CGA GAG TTC TGT GAC CTC CCC CGC 816
Tyr Thr Thr Asp Pro Gln Ile Glu Arg Glu Phe Cys Asp Leu Pro Arg
255 260 265

TGC GGG TCC GAG GCA CAG CCC CGC CAA GAG GCC ACA ACT GTC AGC TGC 864
Cys Gly Ser Glu Ala Gln Pro Arg Gln Glu Ala Thr Thr Val Ser Cys
270 275 280 285

TTC CGC GGG AAG GGT GAG GGC TAC CGG GGC ACA GCC AAT ACC ACC ACT 912
Phe Arg Gly Lys Gly Glu Gly Tyr Arg Gly Thr Ala Asn Thr Thr Thr
290 295 300

GCG GGC GTA CCT TGC CAG CGT TGG GAC GCG CAA ATC CCT CAT CAG CAC 960
Ala Gly Val Pro Cys Gln Arg Trp Asp Ala Gln Ile Pro His Gln His
305 310 315

CGA TTT ACG CCA GAA AAA TAC GCG TGC AAA GAC CTT CGG GAG AAC TTC 1008
Arg Phe Thr Pro Glu Lys Tyr Ala Cys Lys Asp Leu Arg Glu Asn Phe
320 325 330

TGC CGG AAC CCC GAC GGC TCA GAG GCG CCC TGG TGC TTC ACA CTG CGG 1056
Cys Arg Asn Pro Asp Gly Ser Glu Ala Pro Trp Cys Phe Thr Leu Arg
335 340 345

CCC GGC ATG CGC GCG GCC TTT TGC TAC CAG ATC CGG CGT TGT ACA GAC 1104
Pro Gly Met Arg Ala Ala Phe Cys Tyr Gln Ile Arg Arg Cys Thr Asp
350 355 360 365

GAC GTG CGG CCC CAG GAC TGC TAC CAC GGC GCA GGG GAG CAG TAC CGC 1152
Asp Val Arg Pro Gln Asp Cys Tyr His Gly Ala Gly Glu Gln Tyr Arg
370 375 380

GGC ACG GTC AGC AAG ACC CGC AAG GGT GTC CAG TGC CAG CGC TGG TCC 1200
Gly Thr Val Ser Lys Thr Arg Lys Gly Val Gln Cys Gln Arg Trp Ser
385 390 395

GCT GAG ACG CCG CAC AAG CCG CAG TTC ACG TTT ACC TCC GAA CCG CAT 1248
Ala Glu Thr Pro His Lys Pro Gln Phe Thr Phe Thr Ser Glu Pro His
400 405 410

-continued

GCA CAA CTG GAG GAG AAC TTC TGC CGG AAC CCA GAT GGG GAT AGC CAT 1296
Ala Gln Leu Glu Glu Asn Phe Cys Arg Asn Pro Asp Gly Asp Ser His
415 420 425

GGG CCC TGG TGC TAC ACG ATG GAC CCA AGG ACC CCA TTC GAC TAC TGT 1344
Gly Pro Trp Cys Tyr Thr Met Asp Pro Arg Thr Pro Phe Asp Tyr Cys
430 435 440 445

GCC CTG CGA CGC TGC GCT GAT GAC CAG CCG CCA TCA ATC CTG GAC CCC 1392
Ala Leu Arg Arg Cys Ala Asp Asp Gln Pro Pro Ser Ile Leu Asp Pro
450 455 460

CCA GAC CAG GTG CAG TTT GAG AAG TGT GGC AAG AGG GTG GAT CGG CTG 1440
Pro Asp Gln Val Gln Phe Glu Lys Cys Gly Lys Arg Val Asp Arg Leu
465 470 475

GAT CAG CGG CGT TCC AAG CTG CGC GTG GTT GGG GGC CAT CCG GGC AAC 1488
Asp Gln Arg Arg Ser Lys Leu Arg Val Val Gly Gly His Pro Gly Asn
480 485 490

TCA CCC TGG ACA GTC AGC TTG CGG AAT CGG CAG GGC CAG CAT TTC TGC 1536
Ser Pro Trp Thr Val Ser Leu Arg Asn Arg Gln Gly Gln His Phe Cys
495 500 505

GGG GGG TCT CTA GTG AAG GAG CAG TGG ATA CTG ACT GCC CGG CAG TGC 1584
Gly Gly Ser Leu Val Lys Glu Gln Trp Ile Leu Thr Ala Arg Gln Cys
510 515 520 525

TTC TCC TCC TGC CAT ATG CCT CTC ACG GGC TAT GAG GTA TGG TTG GGC 1632
Phe Ser Ser Cys His Met Pro Leu Thr Gly Tyr Glu Val Trp Leu Gly
530 535 540

ACC CTG TTC CAG AAC CCA CAG CAT GGA GAG CCA AGC CTA CAG CGG GTC 1680
Thr Leu Phe Gln Asn Pro Gln His Gly Glu Pro Ser Leu Gln Arg Val
545 550 555

CCA GTA GCC AAG ATG GTG TGT GGG CCC TCA GGC TCC CAG CTT GTC CTG 1728
Pro Val Ala Lys Met Val Cys Gly Pro Ser Gly Ser Gln Leu Val Leu
560 565 570

CTC AAG CTG GAG AGA TCT GTG ACC CTG AAC CAG CGC GTG GCC CTG ATC 1776
Leu Lys Leu Glu Arg Ser Val Thr Leu Asn Gln Arg Val Ala Leu Ile
575 580 585

TGC CTG CCC CCT GAA TGG TAT GTG GTG CCT CCA GGG ACC AAG TGT GAG 1824
Cys Leu Pro Pro Glu Trp Tyr Val Val Pro Pro Gly Thr Lys Cys Glu
590 595 600 605

ATT GCA GGC TGG GGT GAG ACC AAA GGT ACG GGT AAT GAC ACA GTC CTA 1872
Ile Ala Gly Trp Gly Glu Thr Lys Gly Thr Gly Asn Asp Thr Val Leu
610 615 620

AAT GTG GCC TTG CTG AAT GTC ATC TCC AAC CAG GAG TGT AAC ATC AAG 1920
Asn Val Ala Leu Leu Asn Val Ile Ser Asn Gln Glu Cys Asn Ile Lys
625 630 635

CAC CGA GGA CGT GTG CGT GAG AGT GAG ATG TGC ACT GAG GGA CTG TTG 1968
His Arg Gly Arg Val Arg Glu Ser Glu Met Cys Thr Glu Gly Leu Leu
640 645 650

GCC CCT GTG GGG GCC TGT GAG GGT GAC TAC GGG GGC CCA CTT GCC TGC 2016
Ala Pro Val Gly Ala Cys Glu Gly Asp Tyr Gly Gly Pro Leu Ala Cys
655 660 665

TTT ACC CAC AAC TGC TGG GTC CTG GAA GGA ATT ATA ATC CCC AAC CGA 2064
Phe Thr His Asn Cys Trp Val Leu Glu Gly Ile Ile Ile Pro Asn Arg
670 675 680 685

GTA TGC GCA AGG TCC CGC TGG CCA GCT GTC TTC ACG CGT GTC TCT GTG 2112
Val Cys Ala Arg Ser Arg Trp Pro Ala Val Phe Thr Arg Val Ser Val
690 695 700

TTT GTG GAC TGG ATT CAC AAG GTC ATG AGA CTG GGT TAGGCCCAGC 2158
Phe Val Asp Trp Ile His Lys Val Met Arg Leu Gly
705 710

CTTGATGCCA TATGCCTTGG GGAGGACAAA ACTTCTTGTC AGACATAAAG CCATGTTTCC 2218
TCTTTATGCC TGTAAAAAAA AAAAAAAAGA ACGCCCCATG GTGG 2262

GENE ENCODING FOR A L5/3 GROWTH FACTOR AND ITS CDNA

BACKGROUND

Growth factors are important for normal developmental processes, as well as for healing of wounds. Their abnormal expression has been implicated in neoplasia and other proliferative disorders. The kringle-containing protein hepatocyte growth factor (HGF) was originally identified as a potent growth factor involved in liver regeneration after liver injury or partial hepatectomy. It is now known that HGF functions as a growth factor for a broad spectrum of tissues and cell types. In addition, it has been recently discovered that HGF is identical to scatter factor (SF) a cytokine secreted from certain fibroblasts that enhances movement and causes the dissociation and scattering of epithelial cells (Gheradi & Stoker, 1990). The proto-oncogene c--met, a tyrosine kinase, has been found to be the cell surface receptor for HGF (Rubin et al., 1991; Bottaro et al., 1991). These properties may be important for metastasis of tumor cells.

In 1973 it was recognized that serum from partially hepatectomized rats stimulated hepatocyte proliferation in vitro (Morley et al., 1973). One of the agents responsible for this phenomenon was identified and isolated from such serum and from serum of patients with fulminant liver failure (Morley et al., 1973; Michalopoulous et al., 1984; Nakamura et al., 1984; Gohda et al., 1988). This agent was named hepatopoietin A or hepatocyte growth factor (HGF). HGF stimulates hepatocyte DNA synthesis and proliferation. Its serum concentration increases dramatically after rats undergo partial hepatectomy and decreases when the liver regenerates. HGF is produced by non-parenchymal liver cells (Schirmacher et al., 1992) and acts directly on hepatocytes in a paracrine fashion to stimulate cell multiplication. Although HGF stimulates growth of normal hepatocytes, it also has antiproliferative effects on hepatocarcinoma cells in culture (Tajima et al., 1991; Shiota et al., 1992).

HGF is a heterodimer of 82 kD composed of a $\alpha$- and $\beta$-subunit with 51 kD and 26 kD molecular weight, respectively. The cDNAs for human and rat HGF have been cloned and characterized by several groups (Miyazawa et al., 1989; Nakamura et al., 1989; Okajima et al., 1990; Seki et al., 1990; Tashiro et al., 1990; Rubin et al., 1991).

HGF has no obvious homology with other known growth factors but is 38% homologous to plasminogen. It contains four kringle domains followed by a serine protease-like domain where the active site His and Ser have been changed to Gln and Tyr, respectively. HGF has no detectable protease activity. At present the function of the kringle domains in HGF is unknown.

Kringle domains were first identified in bovine prothrombin as an internal duplication of a triple-disulfide--bonded structure containing approximately 80 amino acids (Magnusson et al., 1975). Kringle domains were until recently only characterized in plasma proteins that functioned in blood coagulation or fibrinolysis (Davie et al., 1986) which includes prothrombin, Factor XII, urokinase-type plasminogen activator, tissue-type plasminogen activator and plasminogen. Recently, apolipoprotein(a) and HGF have also been shown to contain kringle domains. Apolipoprotein(a) is thought to be involved in atherosclerosis (McLean et al., 1987). Kringle structures are thought to function autonomously (Trexler & Patthy, 1983; van Zonneveld et al., 1986) and fold independently (Tulinsky et al., 1988).

Kringles appear to be protein-binding domains and have been shown to be essential for the function of prothrombin, plasminogen and tissue plasminogen activator. The functions of all other kringle structures has not been determined, but since these structures are over 50% identical with each other, it is reasonable to assume that they are involved in binding interactions with other proteins essential for their regulation.

Two functional variants of HGF have been identified and have been found to be expressed at variable levels depending on the cell line or tissue being analyzed. A form of HGF containing the aminoterminal end of the protein including the first two kringle domains appears to result from alternative processing of the gene coding for HGF (Chan et al., 1991; Miyazawa et al., 1991). This variant binds to the c-met receptor although not as effectively aS the full-length protein. Another variant has a five amino acid deletion in the first kringle domain that appears to have no effect on its activity (Seki et al., 1990; Rubin et al., 1991). Specific domains in HGF have been deleted by using techniques in molecular biology and the resultant proteins have been studied in various assays where native HGF can be measured. Matsumoto et al. (1991) concluded that the amino-terminal portion of the protein including the first and second kringle domains are essential for biological activity of HGF and possibly binding to the receptor.

Chromosomal abnormalities in a number of neoplastic diseases are sometimes associated with the activation of a proto-oncogene or the loss of a gene that suppresses tumor growth. Growth factors are important for normal developmental processes, as well as healing of wounds. Their abnormal expression has been implicated in neoplasia and other proliferative disorders (Aaronson, 1991). Growth factors are involved in signaling pathways that influence normal cellular differentiation. These proteins cause cells in the resting phase (Go) to enter and progress through the cell cycle. Oncogenic mutations in several growth factors result in unregulated cell growth. Tumor suppressor genes are genes expressed in normal cells that play regulatory roles in cell proliferation, differentiation and other cellular events. Loss or inactivation of these genes is oncogenic. Tumor suppressor genes that have been extensively characterized include the genes for colon carcinoma, retinoblastoma, type 2 neurofibromatosis, the genes involved in Wilms tumor and the p53 gene (reviewed in Weinberg, 1991). Tumor suppressor genes are involved in cell cycle control, signal transduction, anglogenesis, and development (Sager, 1989; Weinberg, 1991).

The concept that the loss of genetic material or the inactivation of a gene plays an important role in human cancer is based on the original observation that somatic cell hybrids between tumor cells and normal cells were no longer tumorigenic. This indicated that normal cells contain genes coding for tumor suppressors whose function was absent in cancer cells. In addition, cytogenic and restriction fragment length polymorphism (RFLP) analyses have established an association between the loss of genetic material on specific chromosomes and the development of various human malignancies.

Deletion of the short arm of human chromosome 3 has been implicated in small cell lung carcinoma (SCLC; Whang-Peng et al., 1982; Naylor et al., 1987), other lung cancers (Kok et al., 1987; Brauch et al., 1987), renal cell carcinoma (Zbar et al., 1987; Kovacs et al., 1988) and yon Hippel-Lindau syndrome (Seizinger et al., 1988) which suggests that one or more tumor suppressor genes reside on chromosome 3p which manifest their transformed phenotype upon their inactivation. The chromosomal locus DNF15S2 (also called D3F15S2) is a RFLP probe that most consistently is associated with loss of heterozygosity in SCLC, being detected in virtually 100% of SCLC.

Lung cancer is a common human malignancy with 150,000 new cases reported each year in the United States. Unfortunately, 90% of affected persons will die within 5 years of diagnosis. Mortality due to lung cancer has increased more than 15% since 1973. Increases in cigarette smoking from 1900 until the early 1960s has transformed lung cancer from a rare disease at the turn of the century to the current leading cause of cancer death. In women, lung cancer surpassed breast cancer as the leading cause of cancer death in 1986 with rates expected to continue to increase for at least another ten years (Henderson et al., 1991).

Lung cancer is divided into small cell and non-small cell varieties. The non-small cell lung cancers include adenocarcinoma, squamous and epidermoid lung cancer and large-cell lung cancer. Chromosome 3p(14–23) changes have been found in nearly all small cell lung cancers and in a large fraction of non-small cell lung cancers.

Cancer of the kidney accounts for 1–2% of all malignancies (excluding skin cancer) with renal cell carcinoma comprising 85% of these. Renal cell carcinoma (RCC) occurs in sporadic and familial forms and are commonly seen in the age group between 50 to 70 years. Cigarette smoking is a known risk factor for this form of cancer (Walter et al., 1989). Deletion of the short arm of chromosome 3 is the most commonly involved region of the genome in RCC and therefore appears to play a role in the development and/or progression of this form of cancer.

Several genes have been localized near or at the D3F15S2 locus. The ERβAB locus coding for a DNA-binding thyroid hormone receptor is localized to human chromosome 3p21–25, and overlaps deletions found in SCLC. Leduc et al. (1989) determined that many non-SCLC tumors retained both ERBAB alleles while the D3F15S2 locus was reduced to homozygosity, ruling out a role for the thyroid hormone receptor in this form of cancer. The gene encoding aminoacylase-1 at 3p21 is inactivated in a large fraction of SCLC (Naylor et al., 1982, 1989). A similar allelic loss is observed in sporadic renal cancers and there are cytogenetic abnormalities of this region in familial renal cell cancer. The gene coding for protein-tyrosine phosphatase7 (PTPγ) maps to 3p21 (LaForgia et al., 1991). This protein and homologous family members reverse the effect of protein tyrosine kinases, of which, some have been identified as oncogenes (ie., met, fms, kit, ERBB). In one study, one PTPγ allele was deleted in 3 of 5 renal carcinoma cell lines and in 5 of 10 lung carcinoma samples tested (LaForgia et al., 1991). In summary, the key gene(s) responsible for tumor suppressor activity at this locus is unknown, although there are some candidate genes.

SUMMARY OF THE INVENTION

The present invention is based on the isolation and characterization of the human gene located at the D3F1552 locus on human chromosome 3 referred to as L5/3. The protein coded for by this gene is referred to as the L5/3 protein. The translated amino acid sequence indicates that L5/3 protein is composed of four kringle structures followed by a serine protease-like domain. This is identical in composition to hepatocyte growth factor (HGF) although L5/3 protein and HGF are only 50% identical to each other when their amino acid sequences are compared. The corresponding human cDNA has also been isolated, as well as the mouse gene and cDNA.

The L5/3 protein can be employed to alter cell growth (as a growth factor or tumor suppressor). The L5/3 protein has properties similar to HGF that is actively involved in liver regeneration.

In addition, the L5/3 gene is identical to the gene at a locus on human chromosome 3 (3p21) that is deleted in DNA from all small cell lung carcinomas and has been hypothesized to contain one or more tumor suppressor genes. Thus this isolated gene L5/3 can be used as a probe to provide an indication of a predisposition for certain cancers. Further, identification of the coded L5/3 protein can also be utilized to evaluate a predisposition to cancer.

BRIEF DESCRIPTION OF THE DRAWINGS

The Figure is a schematic diagram of the amino acid sequence of human L5/3.

DETAILED DESCRIPTION OF THE INVENTION

The methods discussed below to obtain DNA sequences encoding L5/3 are merely for purposes of illustration and are typical of those that might be used. However, other procedures may also be employed.

The human L5/3 gene was isolated using a multistep process employing various DNA and cDNA probes which were both of human and mouse origin. Further, the initial probe is a bovine prothrombin cDNA.

A human liver genomic DNA library cloned into bacteriophage Charon 28 (Lawn et al., 1978) was obtained from Dr. Tom Maniatis, Harvard University (this library is presently available from the ATCC). This library is an Alu/Hae III fetal human genomic DNA library. The library containing approximately $2\times10^6$ recombinant phage was plated out on *E. coli* strain LE392 and grown overnight at 37° C. and was screened by the in situ plaque hybridization technique of Benton & Davis (1977) as modified by Woo (1979).

Approximately $1\times10^8$ cpm of nick-translated bovine prothrombin cDNA probe (obtained by Ava I and Bam HI digestion of pBII102; this probe is 1200 bp in length coding for amino acids 109–500; MacGillivray & Davie, 1984) was hybridized to nitrocellulose filters containing the recombinant phage under conditions of reduced stringency. These conditions included hybridization at 60° overnight in 2×Denhardt's solution (0.04% polyvinylpyrrolidone, 0.04% Ficoll and 0.04% bovine serum albumin) containing 6×SSC [1×SSC: 0.15M sodium chloride and 0,015M trisodium citrate (pH 7.0)], 1 mM EDTA and 0.5% sodium dodecyl sulfate (SDS). The filters were washed three times at 60° C. in 6×SSC with 0.5% SDS. Twelve positive phage were identified. Two of these phage have been identified to code for the human L5 gene.

This human L5 gene and its method of selection is also disclosed in the doctoral thesis of Sandra J. Friezner Degen entitled *Isolation and Characterization*

*of the Human Prothrombin Gene And Related Genes* published in 1982. As discussed below this gene characterized as L5 is an incomplete gene but is useful in isolation and characterization of the gene of the present invention. Until now its function was also unknown.

The obtained L5 gene was then used to obtain the corresponding human L5 cDNA. The human cDNA corresponding to the L5 gene was used to obtain the mouse cDNA. This mouse cDNA was in turn used to obtain the mouse L5/3 gene. The mouse L5/3 gene was used to obtain the human L5/3 gene.

A λgtll cDNA library prepared from human fetal liver mRNA (provided by Dr. Vincent Kidd, University of Alabama, Birmingham; Kwok et al., 1985) was screened for the human cDNA coding for L5 by using a probe isolated from the human L5 gene (680 bp Bam HI and Hind III fragment isolated from a 1850 bp subclone (obtained by digestion of L5 with Hind III and cloning into pBR322) and coding for part of the second kringle and all of the third; nucleotides 2190–2868 of Sequence ID No. 6). Approximately 1×105 phage were screened at high stringency using standard techniques (Degen & Davie, 1987). These conditions include hybridization with the same solution used for isolation of the human L5 gene discussed above but at 68° C. and washing at 68° C. in 1×SSC containing 0.5% SDS. Six positives were identified. The longest (#46) was 1.9 kb in length. A 5′-end fragment from this cDNA (340 bp Eco RI and Nco I fragment coding for part of kringles 1 and 2; nucleotides 388–733 in sequence ID No. 1) was used to rescreen the library to obtain clones with longer 5′ ends. Two clones (#33 and #19) were identified and characterized (Sequence ID No. 1,2,3). The longest clone (#33) is 2200 bp in length excluding the poly(A) tail and is not full-length since its 5′ end starts 16 bp downstream from the putative initiator methionine codon in the first exon of the gene (starting at nucleotide 290 in Sequence ID No. 6).

A λgt10 mouse liver cDNA library (Stratagene, La Jolla, Calif.; from mouse strain C57BL/6) was then screened using a fragment from the human cDNA #33. Approximately $1\times10^6$ phage were screened with a probe isolated from the 5′ end of the human cDNA (the 340 bp fragment was isolated from human cDNA-33 after digestion with Eco RI and Kpn I and coded for the amino-terminal portion of the protein including eight amino acids of the first kringle; nucleotides 1 to 334 in Sequence ID No. 1) using the conditions of reduced stringency discussed above for the isolation of the human L5 gene. These conditions were used to allow for cross species hybridization. Ten positives were identified and eight were characterized after cloning the cDNAs into pBR322.

The longest cDNA (pML5-2) was 2188 bp in length and was not full-length since the open reading frame was present at the 5′ end of the sequence with no codon for the initiator methionine in-frame with the coding sequence (Sequence ID No. 4). After determination of the sequence of the mouse gene it was determined that the cDNA lacked 44 bp of coding and 94 bp of 5′ non-coding sequence at its 5′ end.

A mouse liver genomic DNA library cloned into the Bam HI site of EMBL-3 SP6/T7 (Clontech; mouse strain Balb/c; catalog #M 1030 J) was screened for the gene coding for mouse L5/3. Approximately $1\times10^6$ phage from the library were screened with a probe isolated from the previously isolated mouse cDNA (the 1450 bp insert was isolated from pML5-2 after digestion with Eco RI and coded for eight amino acids of the second kringle, all of the third and fourth kringles and the serine protease-like domain; nucleotides 738 to 2188 in sequence ID No. 4) using the identical high stringency conditions discussed above for the isolation of the human L5 cDNA. On the initial screen, 65 positives were identified; 9 were characterized. Restriction fragments of phage DNA were subcloned into pBR322.

A second human genomic DNA library prepared from placental DNA using EMBL-3 SP6/T7 as the cloning vector (Clontech; catalog #HL 1067 J) was screened for the 5′ end of the gene coding for L5/3 with a mouse genomic fragment containing the first exon of the gene for mouse L5/3. This fragment was 400 bp in length and was isolated by digestion of a genomic subclone from the mouse gene (a 3.3 kb Bgl II fragment cloned into the Bam HI site of pBR322) with Bam HI and Eco RI (nucleotides 1086–1486 in Sequence ID No. 5). Approximately, 500,000 recombinant phage were screened under identical reduced stringency conditions discussed above for the original isolation of the L5 gene. Thirteen positives were identified; three were characterized and found to code for the 5′ end of the human L5/3 gene (referred to as L3).

Fragments from two overlapping phage (L5 and L3) were subcloned into pBR322 and the DNA sequence of the inserts were determined. The entire sequence of the gene present in L5 and L3 is shown in Sequence ID No. 6. This gene is the complete gene L5/3 of the present invention. The gene is 4690 bp in length (from the codon for the putative initiator methionine to the polyadenylation site; nucleotides 274–4963 in Sequence ID No. 6). The gene is composed of 18 exons separated by 17 intervening sequences. In addition, sequence has been determined both upstream and downstream of the gene.

The 3′ end of the acyl-peptide hydrolase gene is 444 base pairs downstream of L5/3 gene on the complementary strand (nucleotides 5408 to 6100 in Sequence ID No. 6).

Several isolated cDNA fragments were characterized. One cDNA (#19) had two parts of the coding region deleted when compared to cDNA (#33) which included nucleotides 1366–1486 and 1565–1613 in Sequence ID No. 1. The cDNA for #19 is Sequence ID No. 3. In the L5/3 gene the region deleted included exon 13 (nucleotides 3532–3652 in Sequence ID No. 6) and the 5′ end of exon 18 (nucleotides 4033–4081 in Sequence ID No. 6). If this cDNA represents a translated mRNA, it would code for the four kringle domains followed by only 22 amino acids since there are two in-frame stop codons at that point.

Comparison of all cDNA sequences indicates that at least five polymorphisms occur; only one of which results in an amino acid substitution. This substitution is a Cys (Sequence ID No. 1) to Phe (Sequence ID No. 2) at amino acid residue 212. When the sequence of the exons in the L5/3 gene are compared to the cDNA sequences, one additional polymorphic site is identified that results in a Tyr (in the cDNAs; Sequence ID No.1 and Sequence ID No. 2) to Cys (in the gene; Sequence ID No. 6) substitution at residue 13. All of these polymorphisms should occur in the population and all would represent functional L5/3 protein.

The gene and cDNA coding for L5/3 codes for a protein with similar domain structure as HGF with four kringles followed by a serine protease-like domain. The translated amino acid sequences of the gene (shown in the Figure) and cDNA for human L5/3 predict a protein with 80,325 molecular weight containing 711 amino acids (excluding additional post-translational processing). The figure is a schematic diagram of the amino acid sequence of human L5/3. The amino acid sequence of human L5/3 is shown starting with residue 1 at the amino-terminal end and ending with residue 711 at the carboxy-terminal end. Placement of disulfide bonds was determined solely on the basis of homology with this protein sequence to plasminogen, where placement of disulfides has been determined. The four kringle domains are indicated by K1, K2, K3, and K4. The region homologous to the preactivation peptide of plasminogen is indicated by PAP. The three potential N-linked cleavage sites are indicated by open arrows. The sequence following the second open arrow is homologous to other serine proteases. The active site amino acids His, Asp and Ser have been changed to Gln, Gln and Tyr, respectively and are indicated in boxes. Amino acids are represented in the one letter code where A-Ala, C=Cys, D=Asp, E=Glu, F=Phe, G=Gly, H=His, I=Ile, K=Lys, L=Leu, M=Met, N=Asn, P=Pro, Q=Gln, R=Arg, S=Ser, T=Thr, V=Val, W=Trp and Y=Tyr. There are three potential carbohydrate additions sites at asparagines in the sequence Asn-X--Thr/Ser at positions 72, 296 and 615 (in the Figure). The sequence at the amino-terminal end of the putative protein is hydrophobic and therefore may be part of a signal sequence required for secretion of the protein from the cell. Comparison of the amino-terminal sequence to a consensus sequence compiled for known signal peptidase cleavage sites (Von Heijne, 1983; Watson, 1984) predicts that the cleavage site could be between residues Gly-31 and Thr-32 (in the Figure). The active protein coded by the L5/3 gene refers to the protein as modified during expression and passage through the cell wall. Thus the active protein would exclude the signal sequence which may include residues 1-31.

Based on homology to plasminogen and other serine proteases, two additional proteolytic cleavage sites are predicted. Between the kringle domain region and the serine protease-like domain is an amino acid sequence that is typically found at the activation sites of other coagulation and fibrinolytic proteins with serine protease activity. Residue 483 is an Arg followed by the sequence Val-Val-Gly--Gly that is typically found at the amino-terminal end of serine proteases (in the Figure). On the basis of this sequence, it is anticipated that active L5/3 protein is proteolytically cleaved to yield a two-chain molecule held together by disulfide bonds or cleaved into two separate polypeptide chains. Amino acid residues 56-103 in human L5/3 are homologous to the preactivation peptide (PAP) in plasminogen and HGF (in the Figure). The PAP region in plasminogen is between the amino-terminal end of the mature protein and the plasmin activation site between Lys-77 and Lys--78. Both lysines are conserved in L5/3 (residues 103 and 104 in the Figure). Cleavage at this site would remove a peptide of 103 amino acids from the protein (including the putative signal peptide) if it is not disulfide-bonded to the remainder of the protein (there is one additional cysteine in this region).

The amino acids found in the active site of serine proteases have been changed from His to Gln, Asp to Gln, and Set to Tyr at positions 522, 568, and 661, respectively (in the Figure). Therefore, we anticipate that this protein has no proteolytic activity.

Only a portion of the entire primary structure may be required for function. Also included within the definition the active proteins coded for by the L5/3 gene are fragments of the entire sequence which retain activity particularly those which result from post-translational processing such as glycosylation. It is further understood that minor modifications of primary amino acid sequence may result in proteins which have substantially equivalent or enhanced activity as compared to any particular illustrated sequence. These modifications may be deliberate, as through site-directed mutagenesis, or may be accidental, such as mutations of hosts which are L5/3 producing organisms. All of these modifications are included as long as the activity of the L5/3 protein is retained.

The complete mouse L5/3 DNA sequence and the amino acid coding regions of the gene are shown in Sequence I.D. No. 5. The mouse L5/3 gene is composed of 18 exons separated by 17 intervening sequences. The gene is 4613 bp in length from the site of initiation of transcription to the polyadenylation site. (Nucleotides 1192 to 5804 in Sequence ID No. 5.) The gene coding for acyl-peptide hydrolase is 410 base pairs downstream of the L5/3 gene, but is transcribed from the complementary strand (nucleotides 6215–6751 in Sequence ID No. 5).

The mouse cDNA (Sequence ID No. 4) codes for a putative protein with the same domain structure as its human homolog with four kringle domains followed by a serine protease-like domain. Translated sequence from the gene and cDNA coding for mouse L5/3 indicate that a protein of 716 amino acids with a molecular weight of 80,593 would be synthesized (excluding any additional post-translational processing). There are four potential N-linked carbohydrate attachment sites at asparagines in the sequence Asn-X--Thr/Ser at positions 72, 173, 305 and 624. The sequence at the amino-terminal end of the putative protein is hydrophobic and therefore may be part of a signal sequence required for secretion of the protein from the cell. Based on homology with the human cDNA the signal peptidase cleavage site is between amino acid residues Gly-31 and Thr--32 Sequence ID No. 4.

There is only one difference found when the sequences of the cDNA and gene coding for mouse L5/3 are compared which results in the substitution of a Gln in the gene (Sequence ID No. 5) to a Pro in the cDNA (Sequence ID No. 4) at residue 19. It is anticipated that this site is polymorphic in the population and that both are representatives of functional L5/3 protein.

The primary site of synthesis of mRNA for L5/3 is in the liver as determined by analysis of rat tissue RNA by Northern analysis. Lesser amounts of L5/3 mRNA were found in the lung, adrenal, and placenta.

A fusion protein was produced as well as polyclonal antibodies. A 968 bp fragment from the human L5/3 cDNA (#33) was obtained after digestion with Bam HI and Bgl II and cloned into the prokaryotic expression vector pUR278 (Ruther & Muller-Hill, 1983). This fragment represents nucleotides 746–1714 in Sequence ID No. 1 and codes for part of kringle 2, all of kringles 3 and 4 and part of the serine protease-like domain of L5/3. In pUR278, the L5/3 cDNA fragment was cloned into the Bam HI site near the 3'end of the lac Z gene to allow for expression of an active $\beta$-galactosidase fused with the peptide encoded by the L5/3 cDNA fragment in *E. coli.* The correct reading frame was maintained in the construct as determined by DNA sequence analysis. The 968 bp insert codes for 321 amino acids (residues 255–576 in Sequence ID No. 1) with a calculated molecular weight of approximately 35,000 daltons. The predicted size for the fusion protein is approximately 151,000 daltons which contains the human L5/3 protein peptide fused to β-galactosidase (116,000 MW).

The fusion protein was isolated and electroeluted after SDS-polyacrylamide gel electrophoresis of isopropyl thiogalactoside (IPTG) induced E.coli cell extract from cells that had been transformed with the fusion construct.

Fusion protein (β-galactosidase/L5/3) was injected into New Zealand rabbits in order to obtain polyclonal antibodies against the fusion protein by standard techniques.

Tissue lysate from human liver and human plasma were electrophoresed on SDS-polyacrylamide gels under reducing condition, transferred to an Immobilon-P membrane (Amersham, Inc.) and reacted with rabbit anti-β-galactosidase/human L5/3 fusion protein serum. The antibody reacted primarily with a polypeptide of approximately 84,000 molecular weight in plasma and to a lesser extent with a polypeptide of 60,000 molecular weight. Non-immune serum did not react with polypeptides of these sizes on either reducing or non-reducing gels. The antibody did not react with any detectable protein in the liver extract. The antibody did not cross react with purified human prothrombin. On nonreducing gels the antibody detected a protein of approximately 90,000 molecular weight.

These results are consistent with the presence of a signal peptide at the amino-terminal of L5/3 that is required for secretion from the cell since the antibody reacted only with a polypeptide present in plasma and not in liver extract. The signal peptide of approximately 3500 daltons would be removed before secretion from the cell. In addition, these results are consistent with proteolysis at possibly both of the putative proteolytic sites present in L5/3 (in the Figure). Based on the translated cDNA sequence, the full-length protein would be approximately 80,000 daltons. Carbohydrate addition to some or all of the three possible N-linked glycosylation sites might increase the molecular weight to the approximately 90,000 dalton size seen in plasma on non-reducing gels. On reducing gels where the disulfide bonds have been removed, the 84,000 molecular weight protein could be the result of proteolytic cleavage between amino acid residues 103 and 104 (Sequence ID No. 1 in the Figure). The predicted size of the protein with the amino-terminal 103 residues removed is approximately 70,000 daltons. The 84,000 molecular weight protein may be this fragment of L5/3 after glycosylation. On non-reducing gels this fragment could possibly be disulfide-bonded to the remainder of the protein (there is one additional cysteine in this part of the protein that could be involved in disulfide formation) and may be the reason why a larger protein was observed on the non-reduced gel compared to the reduced one. The 60,000 dalton polypeptide also seen in plasma on reducing gels could be the result of additional proteolytic cleavage of the protein between residues 483 and 484 (Sequence ID No. 1 in the Figure) which is a typical serine protease activation site. The resultant fragments would have molecular weights of 50,000 and 25,000 daltons (excluding any post-translational modifications such as glycosylation). If the two potential N-linked carbohydrate additions sites in the 50,000 dalton fragment are glycosylated the fragment could be 60,000 daltons in size. The smaller fragment may not have been resolved on this gel or the antibody may not react with it.

These results are analogous to the form of HGF seen in plasma which is a heterodimeric protein of 82,000 daltons composed of α and β subunits of 51,000 and 26,000 daltons, respectively.

A full-length human L5/3 cDNA was then constructed. Since the longest human L5/3 cDNA was not full-length and was missing 16 bp from the 5′ end (Sequence ID No. 1), a full-length L5/3 cDNA was constructed by addition of adaptors. The following complementary oligonucleotides were synthesized: coding: 5′ GCGAATTCCACCATGGGGTGGCTCCCA 3′ complementary 3′ CGCTTAAGGTGGTACCCCACCGAGGGTTTAA 5′

When hybridized to each other this adaptor has the following features: 1) the presence of an Eco RI restriction site (5′ GAATTC 3′) at the 5′ end for cloning into the Eco RI sites in expression vectors; 2) a Kozak consensus sequence surrounding the ATG coding for the initiator methionine (5′ CCACCATGG 3′; Kozak, 1986) to optimize translation from this methionine; 3) an overhanging-end at the 3′ end of the adaptor that is compatible with the EcoRI site present at the 5′ end of the L5/3cDNA-(33) for ligation together; and 4) after ligation of the adaptor to the cDNA insert the Eco RI sites at the ends of the original cDNA will not be reconstituted and therefore the only Eco RI sites will be due to the adaptor.

The 2200 bp cDNA insert from the human L5/3cDNA-(33) was isolated after digestion with Eco RI (nucleotides 1–2219 in Sequence ID No. 1) and ligated to the hybridized oligonucleotides (adaptor). The resulting mixture was digested with Eco RI and electrophoresed on low melting point agarose. The band representing the cDNA with ligated adaptors was excised and the DNA isolated. This DNA was then ligated to the vector Bluescript SK +/− (Stratagene, La Jolla, Calif.), and used to transform *E. coli. E. Coli* transformed with the anticipated full-length L5/3cDNA containing plasmid were initially identified by restriction enzyme digestion of plasmid isolated from white colonies on agar plates containing IPTG, X-Gal and ampicillin (*E. coli* containing the recombinant vector will give white colonies while Bluescript without an insert will give blue colonies). Final confirmation of the full-length construct was determined by DNA sequence analysis.

After adaptor ligation to the human L5/3 cDNA insert there are eight nucleotide differences when the sequence is compared to the exons in the gene for human L5/3 (nucleotides 1301–1312 in Sequence ID No. 6). These are due to the original Eco RI site present at the 5′ end of the L5/3cDNA insert that is the result of linker addition during the construction of the cDNA library and is not naturally present in the cDNA (as determined from the sequence of the gene for this region). These differences result in three amino acid substitutions that we do not anticipate will affect the function of recombinant full-length L5/3 protein since they are present in the proposed signal peptide. The sequence of the full-length construct is shown in Sequence ID No. 7. Residues 6–8 are Leu-Leu-Leu in the gene coding for human L5/3 (Sequence ID No. 6) and Asn-Ser-Val in the full length L5/3 cDNA (Sequence ID No. 7). Adaptor(s) are also present at the 3′ end of the cDNA but should not affect the expression of L5/3 since they are present in the 3' noncoding region of the cDNA.

Mammalian expression vectors were also constructed. The full-length L5/3 insert was isolated from the Bluescript vector after digestion with Eco RI. The insert was then cloned into the Eco RI site of the expression vector pDX. This expression vector was obtained from Dr. Kathy Berkner of Zymogenetics. pDX contains an origin of replication, a SV-40 enhancer, a adenovirus promoter, splice sequences and a polyadenylation signal for appropriate replication and transcription of the inserted cDNA and the accurate synthesis and secretion of the expressed protein. The cDNA provides the signal sequence for secretion. This expression vector has been used to transfect the eukaryotic cell line—Hela which does not normally express L5/3 protein.

Expression in general may be achieved in a variety of host systems including, in particular, mammalian and bacterial systems, as well as yeast based systems. In addition, other cell systems have become available such as the baculovirus vectors used to express protein encoding genes in insect cells. The expression system discussed here is illustrative, and it is understood by those in the art that a variety of expression systems can be used.

Additional factors necessary or helpful in effecting expression may subsequently be identified.

As the nucleotide sequences encoding the human and mouse L5/3 proteins are now available, these may be expressed in a variety of systems. If procaryotic systems are used, an intronless coding sequence should be used, along with suitable control sequences. The cDNA clones for any of the above L5/3 proteins may be excised with suitable restriction enzymes and ligated into procaryotic vectors for such expression. For procaryotic expression of L5/3 genomic DNA, the DNA should be modified to remove the introns, either by site-directed mutagenesis, or by retrieving corresponding portions of cDNA and substituting them for the intron-containing genomic sequences. The intronless coding DNA is then ligated into expression vectors for procaryotic expression.

As discussed above, L5/3 encoding sequences may also be used directly in an expression system capable of processing the introns, usually a mammalian host cell culture. To effect such expression, the genomic sequences can be ligated downstream from a controllable mammalian promoter which regulates the expression of these sequences in suitable mammalian cells.

E. coli RRI cells carrying the plasmid containing L5/3cDNA (#33) exhibited in Sequence ID No. 1 has been deposited with the American Type Cell Culture in Rockville, Md. and is designated ATCC No. 68976 (deposited on May 6, 1992).

The gene sequence No. 1 submitted below is useful of course when labeled by for example Nick translation as a probe for the D3F15S2 locus on human chromosome 3. This is significant with respect to detection of mutations which provide an indication of one's predisposition to lung carcinoma, renal cell carcionoma and Von Hipple-Lindau syndrome. Further, the protein coded by the DNA and associated cDNA is useful as an in vitro growth promoter particularly for hepatocytes. This can be used to alter growth characteristics of hepatocytes by combining minor amounts (0.1 to 100 nanograms) of the protein per milliliter of growth serum with hepatocytes.

Further the antibody to the L5/3 protein is useful for detection of the L5/3 protein in human serum. This again is useful for the purpose of again detecting any alteration of the chromosome 3 locus D3F15S2 and again an indication of the predisposition towards cancer.

Further, cited below are the DNA sequences for both the human and the mouse along with the cDNA sequences for the human and mouse and the protein associated with the human DNA.

Sequence ID No. 1: cDNA for Human L5/3 clone #33 and associated protein.

Sequence ID No. 2: cDNA for Human L5/3 clone #33 with polymorphism relative to Sequence ID No. 1 and associated protein.

Sequence ID No. 3: cDNA for Human L5/3 clone #19 and associated protein.

Sequence ID No. 4: cDNA for Mouse L5/3 and associated protein.

Sequence ID No. 5: DNA for Mouse L5/3 and associated protein.

Sequence ID No. 6: DNA Sequence of Human L5/3 and associated protein.

Sequence ID No. 7: cDNA Sequence of Human L5/3 with 5' and 3' adaptors added to make a full length cDNA.

I claim:

1. A purified isolated DNA sequence from D3F15S2 locus on human chromosome 3 consisting essentially of 18 exons coding for a human growth factor said human growth factor comprising an approximately 80,000 dalton protein containing four kringle units.

2. The DNA sequence of claim 1 having the sequence identified in Seq. I.D. No. 6.

3. The DNA sequence of claim 1 which is a cDNA sequence.

4. The cDNA sequence of claim 3 having the sequence identified in Seq. I.D. No. 7.

* * * * *